US008329445B2

(12) United States Patent
Frost

(10) Patent No.: US 8,329,445 B2
(45) Date of Patent: *Dec. 11, 2012

(54) BIOSYNTHESIS OF PHLOROGLUCINOL AND PREPARATION OF 1,3-DIHYDROXYBENZENE THEREFROM

(75) Inventor: John W. Frost, Okemos, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/081,993

(22) Filed: Apr. 7, 2011

(65) Prior Publication Data

US 2011/0183391 A1    Jul. 28, 2011

Related U.S. Application Data

(60) Division of application No. 11/784,452, filed on Apr. 6, 2007, now Pat. No. 7,943,362, which is a continuation of application No. PCT/US2005/036291, filed on Oct. 11, 2005.

(60) Provisional application No. 60/617,959, filed on Oct. 12, 2004, provisional application No. 60/618,024, filed on Oct. 12, 2004.

(51) Int. Cl.
*C12N 1/20* (2006.01)
*C12N 15/00* (2006.01)
*C12N 9/00* (2006.01)
*C12P 21/06* (2006.01)
*C12P 7/22* (2006.01)
*C07H 21/04* (2006.01)
*C07K 1/00* (2006.01)

(52) U.S. Cl. ........... 435/252.3; 435/252.33; 435/252.34; 435/254.11; 435/320.1; 435/69.1; 435/183; 435/156; 536/23.1; 536/23.2; 530/350

(58) Field of Classification Search ............... 435/252.3, 435/252.33, 252.34, 254.11, 320.1, 69.1, 435/183, 156; 536/23.1, 23.2; 530/350
See application file for complete search history.

(56) References Cited

U.S. PATENT DOCUMENTS

| 2,246,963 | A |   | 6/1941  | Wilkinson        |
|-----------|---|---|---------|------------------|
| 4,760,048 | A |   | 7/1988  | Kurihara et al.  |
| 5,350,576 | A |   | 9/1994  | Payne et al.     |
| 6,051,383 | A |   | 4/2000  | Thomashow et al. |
| 6,194,167 | B1 |  | 2/2001  | Browse et al.    |
| 6,322,820 | B1 |  | 11/2001 | Simoneau         |
| 6,767,744 | B2 |  | 7/2004  | Koffas et al.    |
| 6,774,107 | B1 |  | 8/2004  | Strittmatter et al. |
| 6,783,758 | B2 |  | 8/2004  | Wands et al.     |
| 6,790,639 | B2 |  | 9/2004  | Brown et al.     |
| 7,943,362 | B2 | * | 5/2011  | Frost .......................... 435/252.3 |

FOREIGN PATENT DOCUMENTS

| GB | 1 182205      | 2/1970  |
|----|---------------|---------|
| GB | 1278576       | 6/1972  |
| GB | 1 509358      | 5/1978  |
| JP | 5-239422      | 9/1993  |
| WO | WO 99/26479   | 6/1999  |
| WO | WO 00/71110   | 11/2000 |
| WO | WO 2006/044290 | 4/2006 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Kimchi-Sarfaty et al., A "Silent" polymorphism in the MDR1 gene changes substrate specificty. Science, 2007, vol. 315: 525-528.*
Nackley et al., Human Caechol-O-Methytransferase haplotypes modulate protein expression by altering mRNA secondary structure. Science, 2006, vol. 314: 1930-1933.*
Sauna et al., Silent polymorhisms speak: How they affect pharmacogenomics and the treatment of cancer. Cancer Res., 2007, vol. 67(20): 9609-9612.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
McSpadden Gardener, B., et al., "A Rapid Polymerase Chain Reaction-Based Assay Characterizing Rhizosphere Populations of 2,4-Diacetylphloroglucinol-Producing Bacteria," Phytopathology, 91(1):44-54, (Jan. 2001).
Moore, B. and Hopke, J., "Discovery of a New Bacterial Polyketide Biosynthetic Pathway," Chembiochem, 2(1):35-38, (Jan. 5, 2001).
Brown, N., et al., Bioinformatics: Application Note, 14:380-381 (1998).
Jez, J., et al., Chem. Bio, 7:919-930, (2000).
Kambourakis, et al., J. Am. Chem. Soc., 122:9042 (2000).
Ran, N., et al., J. Am. Chem. Soc., 123:10927, (2001).
Vallari, D., et al., J. Biol. Chem., 262:2468 (1987).
Abbas, A., et al., J. Bacteriol., 184:3008, (2002).
Abbas, A., et al., Microbiology, 150:2443, (2004).
Achkar, J., et al., "Biosynthesis of phloroglucinol," Journal of the American Chemical Society, 127(15):5332-5333, (Apr. 2005).
Agatep, R., et al., Technical Tips Online, 1:01525, (1998).
Austin, M., et al., Nat. Prod. Rep., 20:79-110, (2003).

(Continued)

*Primary Examiner* — Ganapathirama Raghu
(74) *Attorney, Agent, or Firm* — Harness, Dickey & Pierce, P.L.C.

(57) ABSTRACT

The present invention provides methods, enzymes, and cells for the biosynthetic production of phloroglucinol from malonyl-CoA, which is ultimately obtained from simple starting materials such as glucose; also provided are methods for preparing derivatives of biosynthetic phloroglucinol, including, e.g., resorcinol.

15 Claims, 4 Drawing Sheets

OTHER PUBLICATIONS

Bangera M Gita, et al., "Identification and characterization of a gene cluster for synthesis of the polyketide antibiotic 2,4-diacetylphloroglucinol from *Pseudomonas fluorescens* Q2-87," Journal of Bacteriology, 181(10):3155-3163, (May 1999).
Baas, D. et al., Eur. J. Biochem., 265:896-901, (1999).
Beck, J., et al., Eur. J. Biochem, 192:487, (1990).
Brown, N.P., et al., Bioinfonnatics: Application Note, 14:380-381, (1998).
Chen, et al., Biochemistry, 29:1112, (1990).
Davis, M., et al., J. Biol. Chem., 275:28593, (2000).
Delany, I., et al., Microbiol., 146:537, (2000).
Draths, K., et al., J. Am. Chem. Soc., 117:2395, (1995).
Eckemann, S., et al., Nature, 396:387, (1998).
Gibson, J., et al., Angew. Chem., Int. Ed., 40:1945, (2001).
Hansen, Chad A., et al., "Deoxygenation of polyhydroxybenzenes: an alternative strategy for the benzene-free synthesis of aromatic chemicals," Journal of the American Chemical Society, 124(21):5926-5927, (May 2002).
Hansen, Chad A, "Cherne-Enzymatic Synthesis of Aromatics via Non-Shikmate Pathway Intmediates," PhD Thesis Chapter 3-4, Michigan State University, (2002).
Jez, J., et al., Chern. Bio., 7:919-930, (2000).
Kambourakis, et al., J. Am. Chern. Soc., 122:9042, (2000).
Krumenacker, L., et al., Kirk-Othmer Encyclopedia of Chemical Technology, J.I. Kroschwitz & M. Howe-Grant, eds., 13:996, (4th ed., 1995).
Ma, H., et al., Gene., 58:201-216, (1987).
Meurer, G., et al., Mol. Gen. Genet., 232:106-116, (1992).
Mumberg, D., et al., Gene., 156:119-122, (1995).
Novak-Thompson, B., et al., Can. J. Microbiol., 40:1064, (1994).
Paulsen, Ian T. et al., "Complete genome sequence of the plant commensal *Pseudomonas fluorescens* Pf-5," Nature Biotechnology, 23(7):873-878, (Jul. 2005).
Pichuantes, S., et al., in Protein engineering: Principles and Practice; Cleland, J.L.; Craik, C.S., Eds.; Wiley-Liss, Chapter 5:129-161, (1996).
Ramette, A, et al., Plant-Microbe Interact, 14:639, (2001).
Ran, N., et al., J. Am. Chern. Soc., 123:10927, (2001).
Rescigno, M., et al., Biochemistry, 33:5721, (1994).
Reid, et al., "A model of structure and catalysis for ketoreductase domain in modular polyketide synthases," Biochemistry, 42:72-79, (2003).
Richardson, et al., Metab. Eng., 1:180, (1999).
Romanos, M., et al., Yeast., 8: 423-488, (1992).
Schnider-Keel, U., et al., J. Bacteriol., 182:1215, (2000).
Schoefer, L. et al., Appl. Environ. Microbiol., 70(10):6131-6137, (2004).
Schorr, et al., J. Plant Physiol., 143:407, (1994).
Seffernick et al., J. Bacteriol., 183(8):2405-2410, (2001).
Shanahan, P., et al., Anal. Chim Acta, 272:271, (1993).
Spencer, et al., Biochem J., 288:839, (1992).
Takamura, et al., J. General Microbiol., 134:2249, (1988).
Vadali, R., et al., Metab. Eng., 6:133-139, (2004).
Vallari, D., et al., J. Biol. Chern., 262:2468, (1987).
Witkowski et al., Biochemistry 38:11643-11650, (1999).
Zha, W., et al., "Rational pathway engineering of type I fatty acid synthase allows the biosynthese of triacetic acid lactone from D-glucose in vivo," J. American Chemical Society, 126(14):4534-4535, (Apr. 2004).
Database Embl. (Online), "*Pseudomonas fluorescens* phID gene for PhID, complete cds.," Database accession No. AB125213, (Oct. 30, 2003).
Database Embl. (Online), "*Pseudomonas fluorescens* strain Pf5 putative polyketide synthase PhID (PhID) gene, partial cds.," Database accession No. AF214457, (Dec. 29, 1999).
Database Embl. (Online), "*Pseudomonas fluorescens* 2,4-diacetylphloroglucinol biosynthesis genes: PhlE (PhlE), PhID (PhID), PgIB (Phl B), PhlC (ph l C), PhlA (PhlA), PhlF (PhlF) genes, complete cds.," Database accession No. U41818, (Jan. 26, 1996).
International Search Report in International App. No. PCT/US2005/036291, Sep. 22, 2006.
International Preliminary Report on Patentability in International App. No. PCT/US2005/036291, Feb. 19, 2007.
Office Action in U.S. Appl. No. 11/784,452 mailed May 25, 2010.
Office Action in U.S. Appl. No. 11/784,452 mailed May 28, 2010.
Notice of Allowance in U.S. Appl. No. 11/784,452 mailed Feb. 4, 2011.

* cited by examiner

SEQUENCE LISTING

```
<160> NUMBER OF SEQ ID NOS: 2

<210> SEQ ID NO 1
<211> LENGTH: 1050
<212> TYPE: DNA
<213> ORGANISM: Pseudomonas fluorescens Pf-5
<220> FEATURE:
<221> NAME/KEY: CDS
<222> LOCATION: (1)..(1050)
<223> OTHER INFORMATION: Phloroglucinol synthase ORF

<400> SEQUENCE: 1 atg tct aca ctt tgc ctt cca cac gtc atg ttt ccg caa cac aag atc        48
Met Ser Thr Leu Cys Leu Pro His Val Met Phe Pro Gln His Lys Ile
1               5                   10                  15 acc cag caa cag atg gtc gat cac ctg gaa aac ctg cac gcc gac cat        96
Thr Gln Gln Gln Met Val Asp His Leu Glu Asn Leu His Ala Asp His
            20                  25                  30 cca cgc atg gcc ctg gcc aag cgc atg atc gcc aac acc gaa gtc aac       144
Pro Arg Met Ala Leu Ala Lys Arg Met Ile Ala Asn Thr Glu Val Asn
```

```
                35                   40                     45
gag cgc cac ctg gtg ttg ccg atc gac gaa ctg gca gtg cac acc ggt    192
Glu Arg His Leu Val Leu Pro Ile Asp Glu Leu Ala Val His Thr Gly
 50                  55                     60 ttc acc cac cgc agc atc gtc tac gag cgt gaa gcc cgg cag atg tcg    240
Phe Thr His Arg Ser Ile Val Tyr Glu Arg Glu Ala Arg Gln Met Ser
 65                  70                     75                 80 tcg gcc gcg gcg cgc cag gcc atc gag aat gcc ggg ctg cag atc agc    288
Ser Ala Ala Ala Arg Gln Ala Ile Glu Asn Ala Gly Leu Gln Ile Ser
                 85                     90                 95 gac att cgc atg gtc atc gtc act tcc tgc acc ggc ttc atg atg ccg    336
Asp Ile Arg Met Val Ile Val Thr Ser Cys Thr Gly Phe Met Met Pro
            100                    105                110 tcg ctg acc gcg cac ctg atc aac gac ctg gcc ctg cca acc tcc acc    384
Ser Leu Thr Ala His Leu Ile Asn Asp Leu Ala Leu Pro Thr Ser Thr
        115                    120                    125 gtg cag ttg ccg atc gcc cag ctg ggc tgc gtg gcc ggt gcc gcg gcc    432
Val Gln Leu Pro Ile Ala Gln Leu Gly Cys Val Ala Gly Ala Ala Ala
130                    135                    140 atc aac cgc gcc aac gac ttc gcc cgg ctc gat gcc cgc aac cac gta    480
Ile Asn Arg Ala Asn Asp Phe Ala Arg Leu Asp Ala Arg Asn His Val
145                    150                    155                160 ctg atc gtg tcc ctg gaa ttc tcc tcg ctg tgc tac cag ccg gac gac    528
Leu Ile Val Ser Leu Glu Phe Ser Ser Leu Cys Tyr Gln Pro Asp Asp
                165                    170                    175 acc aag ctg cac gcc ttc atc tcc gcg gcg ctg ttc ggc gat gcg gta    576
Thr Lys Leu His Ala Phe Ile Ser Ala Ala Leu Phe Gly Asp Ala Val
            180                    185                    190 tcc gcc tgc gtg ctg cgc gcc gat gac cag gcc ggc ggc ttc aag atc    624
Ser Ala Cys Val Leu Arg Ala Asp Asp Gln Ala Gly Gly Phe Lys Ile
        195                    200                    205 aag aag acc gag tcg tac ttc ctg ccc aag agc gag cac tac atc aag    672
Lys Lys Thr Glu Ser Tyr Phe Leu Pro Lys Ser Glu His Tyr Ile Lys
210                    215                    220 tac gac gtg aag gac acc ggc ttt cac ttc acc ctc gac aag gcg gtg    720
Tyr Asp Val Lys Asp Thr Gly Phe His Phe Thr Leu Asp Lys Ala Val
225                    230                    235                240 atg aac tcc atc aag gac gtg gca ccg gtc atg gag cgg ctc aac tac    768
Met Asn Ser Ile Lys Asp Val Ala Pro Val Met Glu Arg Leu Asn Tyr
                245                    250                    255 gag agc ttc gaa cag aac tgt gcg cac aac gac ttc ttc atc ttc cac    816
Glu Ser Phe Glu Gln Asn Cys Ala His Asn Asp Phe Phe Ile Phe His
            260                    265                    270 acc ggt ggt cgc aag atc ctc gac gag ctg gtg atg cac ctg gac ctg    864
Thr Gly Gly Arg Lys Ile Leu Asp Glu Leu Val Met His Leu Asp Leu
        275                    280                    285 gca tcc aac cgg gtc tcg caa tcg cgc agc agc ctg tcg gaa gcc ggc    912
Ala Ser Asn Arg Val Ser Gln Ser Arg Ser Ser Leu Ser Glu Ala Gly
290                    295                    300 aac att gcc agc gtg gtg gtg ttc gac gta ctc aag cgg cag ttc gat    960
Asn Ile Ala Ser Val Val Val Phe Asp Val Leu Lys Arg Gln Phe Asp
305                    310                    315                320 tcc aac ctc aat cgc ggc gac atc ggc ctg ctg gca gcc ttc ggc ccg   1008
Ser Asn Leu Asn Arg Gly Asp Ile Gly Leu Leu Ala Ala Phe Gly Pro
                325                    330                    335 ggg ttc acc gcg gaa atg gcg gtg ggc gag tgg acc gcc tga           1050
Gly Phe Thr Ala Glu Met Ala Val Gly Glu Trp Thr Ala
            340                    345
```

<210> SEQ ID NO 2

<211> LENGTH: 349
<212> TYPE: PRT
<213> ORGANISM: Pseudomonas fluorescens Pf-5

<400> SEQUENCE: 2

```
Met Ser Thr Leu Cys Leu Pro His Val Met Phe Pro Gln His Lys Ile
1               5                   10                  15

Thr Gln Gln Met Val Asp His Leu Glu Asn Leu His Ala Asp His
            20                  25                  30

Pro Arg Met Ala Leu Ala Lys Arg Met Ile Ala Asn Thr Glu Val Asn
            35                  40                  45

Glu Arg His Leu Val Leu Pro Ile Asp Glu Leu Ala Val His Thr Gly
    50                  55                  60

Phe Thr His Arg Ser Ile Val Tyr Glu Arg Glu Ala Arg Gln Met Ser
65                  70                  75                  80

Ser Ala Ala Arg Gln Ala Ile Glu Asn Ala Gly Leu Gln Ile Ser
                85                  90                  95

Asp Ile Arg Met Val Ile Val Thr Ser Cys Thr Gly Phe Met Met Pro
                100                 105                 110

Ser Leu Thr Ala His Leu Ile Asn Asp Leu Ala Leu Pro Thr Ser Thr
            115                 120                 125

Val Gln Leu Pro Ile Ala Gln Leu Gly Cys Val Ala Gly Ala Ala Ala
            130                 135                 140

Ile Asn Arg Ala Asn Asp Phe Ala Arg Leu Asp Ala Arg Asn His Val
145                 150                 155                 160

Leu Ile Val Ser Leu Glu Phe Ser Ser Leu Cys Tyr Gln Pro Asp Asp
                165                 170                 175

Thr Lys Leu His Ala Phe Ile Ser Ala Ala Leu Phe Gly Asp Ala Val
            180                 185                 190

Ser Ala Cys Val Leu Arg Ala Asp Asp Gln Ala Gly Phe Lys Ile
            195                 200                 205

Lys Lys Thr Glu Ser Tyr Phe Leu Pro Lys Ser Glu His Tyr Ile Lys
210                 215                 220

Tyr Asp Val Lys Asp Thr Gly Phe His Phe Thr Leu Asp Lys Ala Val
225                 230                 235                 240

Met Asn Ser Ile Lys Asp Val Ala Pro Val Met Glu Arg Leu Asn Tyr
                245                 250                 255

Glu Ser Phe Glu Gln Asn Cys Ala His Asn Asp Phe Phe Ile Phe His
            260                 265                 270

Thr Gly Gly Arg Lys Ile Leu Asp Glu Leu Val Met His Leu Asp Leu
            275                 280                 285

Ala Ser Asn Arg Val Ser Gln Ser Arg Ser Ser Leu Ser Glu Ala Gly
            290                 295                 300

Asn Ile Ala Ser Val Val Val Phe Asp Val Leu Lys Arg Gln Phe Asp
305                 310                 315                 320

Ser Asn Leu Asn Arg Gly Asp Ile Gly Leu Leu Ala Ala Phe Gly Pro
                325                 330                 335

Gly Phe Thr Ala Glu Met Ala Val Gly Glu Trp Thr Ala
            340                 345
```

BIOSYNTHESIS OF PHLOROGLUCINOL AND PREPARATION OF 1,3-DIHYDROXYBENZENE THEREFROM

CROSS-REFERENCE TO RELATED APPLICATIONS

The present application is a divisional application of U.S. patent application Ser. No. 11/784,452, filed Apr. 6, 2007, now U.S. Pat. No. 7,943,362 B2, issued May 17, 2011, which is a continuation of International Application No. PCT/US2005/036291, filed Oct. 11, 2005, which claims the benefit of and priority to U.S. Provisional Application Serial Nos. 60/617,959 and 60/618,024, both filed Oct. 12, 2004, the entire contents of which applications are hereby incorporated by reference into the present application.

STATEMENT OF GOVERNMENT INTEREST

This invention was made in part with Government support under Grant No. N00014-02-1-0725, awarded by the Office of Naval Research. The government may have certain rights in this invention.

BACKGROUND

Phloroglucinol (1,3,5-trihydroxybenzene) and its derivatives are widely used in commerce. Phloroglucinol and its derivatives, e.g., trimethylphloroglucinol, are used as pharmaceutical agents, e.g., as antispasmodics. Phloroglucinol is used as a starting material or intermediate in pharmaceutical, microbicide, and other organic syntheses. Phloroglucinol is used as a stain for microscopy samples that contain lignin (e.g., wood samples), and it is used in the manufacture of dyes, including leather, textile, and hair dyes. It is used in the manufacture of adhesives and as an epoxy resin curing agent, and in the preparation of explosives, e.g., the thermally- and shock-stable high explosive, 1,3,4-triamino-2,4,6-trinitrobenzene (TATB). Phloroglucinol also functions as an antioxidant, stabilizer, and corrosion resistance agent, and is utilized as a coupling agent for photosensitive duplicating paper, as a substitute for silver iodide in rain-making, as a bone sample decalcifying agent, and as a floral preservative. Phloroglucinol can also be converted to resorcinol by catalytic hydrogenation.

Resorcinol (1,3-dihydroxybenzene) is a particularly useful derivative of phloroglucinol, although resorcinol is not currently produced by that route. As is phloroglucinol, resorcinol is used in the manufacture of dyes and adhesives, and as an epoxy resin curing agent; and it is used as a starting material or intermediate in pharmaceutical and other organic syntheses. Resorcinol and its derivatives are further commonly used, either alone or with other active ingredients such as sulfur, in cosmetics and in topical skin medicaments for treatment of conditions including acne, dandruff, eczema, and psoriasis, functioning, in part, as an antiseptic and antipruritic. Resorcinol is also used as a cross-linking agent for neoprene, as a tack-enhancing agent in rubber compositions, in bonding agents for organic polymers (e.g., melamine and rubber), and in the fabrication of fibrous and other composite materials. Resorcinol is used: in the manufacture of resins and resin adhesives, e.g., both as a monomer and as a UV absorbing agent; in the manufacture of explosives, e.g., energetic compounds such as styphnic acid (2,4,6-trinitrobenzene-1,3-diol) and heavy metal styphnates; and in the synthesis of diazo dyes, plasticizers, hexyl resorcinol, and p-aminosalicylic acid.

The most common of the resorcinol-based resins are resorcinol-aldehyde and resorcinol-phenol-aldehyde resins. These types of resorcinol-based resins are used, for example, as resin adhesives, composite material matrices, and as starting materials for rayon and nylon production. Examples of composite materials include resorcinol-formaldehyde carbon (or other organic) particle hydrogels, aerogels, and xerogels, which are useful, e.g., as matrix materials for metallic and organometallic catalysts. Resorcinol-formaldehyde resins and particulate composites therewith are also used in dentistry as a root canal filling material.

Resorcinol-aldehyde resin adhesives are especially useful in applications requiring high bond strength, including, e.g.: wooden trusses, joists, barrels, and boats; and aircraft. Modified resorcinol-aldehyde resin adhesives are also used as biological wound sealant compositions both on topical wounds and on internal wounds or surgical cuts, e.g., vascular incisions. This is often done in military field medicine, e.g., to minimize environmental exposure, reduce bleeding and fluid loss, and speed the healing process. Such modified resin adhesives include, e.g., gelatin-resorcinol-formaldehyde and gelatin-resorcinol-glutaraldehyde compositions, wherein the aldehyde may be maintained separately from, and later mixed with, the resorcinol-gelatin composition to form the sealant when needed.

Currently, both phloroglucinol and resorcinol are commercially produced by chemical organic synthesis using caustics and high temperatures, beginning with petroleum-derived starting materials and creating much environmentally problematic waste.

As a result, it would be an improvement in the art to provide more efficient and cleaner processes for the production of these valuable compounds. One possible solution might be to provide a biosynthetic route for production of phloroglucinol, with an optional hydrogenation of the biosynthetic phloroglucinol to resorcinol. Biosynthetic production of compounds related to phloroglucinol has been reported in plants, algae, and microbes, e.g.: acetyl phioroglucinols from *Pseudomonas* spp.; hyperforins, hyperfoliatins, hyperjovinols, and hyperatomarins from *Hypericum* spp.; pallidusol, dehydropallidusol, pallidol, mallopallidol, and homomallopallidol from *Mallotus* spp.; garcinielliptones from *Garcinia* spp.; flavaspidic acids from *Dryopteris* spp.; macrocarpals and sideroxylonals from *Eucalyptus* spp.; 1,3,5-trimethoxybenzene from *Rosa* spp.; as well as phloroglucinol-containing glycosides and phlorotannins.

However, production of phloroglucinol is reported in such plants and microbes as merely a degradation product of more complex, and thus less abundant and/or more costly, starting materials. See, e.g.: L. Schoefer et al., *Appl. Environ. Microbiol.* 70(10):6131-37 (2004); D. Baas & J. Rétey, *Eur. J. Biochem.* 265:896-901 (1999). In addition, microbial biosynthetic production of di-acetyl phioroglucinols has been proposed as a means for improving the anti-fungal activity of recombinant bacteria to be released into the agricultural environment as biocontrol agents against phytopathogens. See U.S. Pat. No. 6,051,383, Thomashow et al., issued Apr. 18, 2000; and M. G. Bangera & L. S. Thomashow, *J Bact.* 181 (10):3155-63 (1999). Yet, a route of anabolic biosynthetic production of phloroglucinol, e.g., from inexpensive starting materials such as glucose, is not shown.

Recently, an alternate route (see FIG. 2) to phloroglucinol (1a) has been elaborated, which involves microbe-catalyzed synthesis of triacetic acid lactone (3a) from glucose; however, it has been found that multiple chemical steps are needed to convert triacetic acid lactone (3a) into phloroglucinol (1a). See W. Zha et al., *J. Am. Chem. Soc.* 126(14):4534-35 (2004);

and C. A. Hansen & J. W. Frost, *J. Am. Chem. Soc.* 124(21): 5926-27 (2002). Thus, this route is at best a partly biosynthetic, partly chemosynthetic pathway.

Thus, to date, no fully biosynthetic route useful for commercial production of phloroglucinol per se (1,3,5-trihydroxybenzene) has been reported. No enzymes or encoding genes that catalyze the formation of phloroglucinol per se have been identified.

SUMMARY

The present invention provides methods, enzymes, and cells for the biosynthetic production of phloroglucinol from malonyl-CoA, and ultimately from simple starting materials such as glucose. Specifically, the present invention provides the first entirely biosynthetic, anabolic route for phloroglucinol synthesis that does not require all four of the phlABCD operon enzymes, but is capable of commercial phloroglucinol production using only a phlD enzyme or other phloroglucinol synthase. Also provided are methods for preparing derivatives of biosynthetic phloroglucinol, including, e.g., resorcinol. Uses of the enzyme systems, recombinant cells, and methods, for production of phloroglucinol; phloroglucinol produced thereby. Uses of the enzyme systems, recombinant cells, and methods, for production of phloroglucinol derivative(s), e.g., resorcinol; phloroglucinol and derivatives, e.g., resorcinol, produced thereby. Uses of the enzyme systems, recombinant cells, methods, phloroglucinol, or derivative(s) for production of compounds or compositions, e.g., explosive or propellant compounds and compositions; uses of the enzyme systems, recombinant cells, methods, phloroglucinol, or derivative(s) for production of non-explosive, non-propellant compounds and compositions, such as medicament, cosmetic, dye, polymer resin, rubber, adhesive, sealant, coating, composite material, or laminated or bonded materials. Explosive or propellant compounds and compositions produced thereby; non-explosive, non-propellant compounds and compositions produced thereby. The present invention further provides:

Isolated or recombinant PhlD+ enzyme systems that are at least one of PhlA−, PhlB−, or PhlC−; PhlD+ recombinant cells that are at least one of PhlA−, PhlB−, or PhlC−; and PhlD+ recombinant cells that have been genetically engineered to increase the expression of PhlD therein;, which enzyme systems and recombinant cells are capable of converting malonyl-CoA to phloroglucinol; such enzyme systems and cells that are PhlA−, PhlB−, and PhlC−; such enzyme systems and cells that further comprise at least one malonyl-CoA synthesis enzyme;

Processes for production of anabolic phloroglucinol involving providing such an enzyme system or recombinant cell and malonyl-CoA or another carbon source that the enzyme system or recombinant cell is capable of converting to malonyl-CoA, contacting either the malonyl-CoA with the enzyme system or recombinant cell under conditions in which it can synthesize phloroglucinol therefrom, or the other carbon source with the enzyme system or recombinant cell under conditions in which it can convert the carbon source to malonyl-CoA and can synthesize phloroglucinol therefrom; such processes in which the carbon source is a simple carbon source, such as saccharide, an aliphatic polyol, or a combination thereof; such processes in which the cell is cultured in a medium containing the carbon source, or where the culturing is performed as an extractive fermentation, and/or where the culturing utilizes a multi-temperature profile, such as a dual-temperature profile; phloroglucinol prepared by such processes;

Isolated or recombinant phloroglucinol synthase enzymes capable of converting malonyl-CoA to phloroglucinol; such enzymes comprising an amino acid sequence of SEQ ID NO:2, or an amino acid sequence that is at least 70% homologous to SEQ ID NO:2, such as a conservatively substituted variant of the amino acid sequence of SEQ ID NO:2;

Isolated or recombinant nucleic acids comprising at least one open reading frame encoding a PhlD enzyme, and that is at least one of phlA−, phlB−, or phlC−; such nucleic acids further comprises at least one open reading frame encoding a malonyl-CoA synthesis enzyme; such nucleic acids in which the PhlD-encoding ORF comprises a base sequence of, or at least 80% homologous to, SEQ ID NO:1, an RNA base sequence corresponding thereto, or a codon sequence redundant therewith;

phlD+ recombinant cells that have been transformed with such a nucleic acid, from which the cell can express phloroglucinol synthase; such cells that are at least one of phlA−, phlB−, or phlC−; such cells that are phlA−, phlB−, and phlC−; such cells that are further at least one of phlE− or phlF;

Processes for the preparation of resorcinol involving providing such anabolic phloroglucinol biosynthesized by such an isolated or recombinant enzyme system or recombinant cells, along with hydrogen and a rhodium catalyst, and contacting the phloroglucinol with the hydrogen and the rhodium catalyst under conditions in which the phloroglucinol is hydrogenated to form resorcinol; resorcinol prepared from such anabolic phloroglucinol;

Uses of such anabolic phloroglucinol, or of resorcinol prepared therefrom, in the manufacture of a medicament, cosmetic, dye, polymer resin, rubber, adhesive, sealant, coating, composite material, or laminated or bonded material; medicament, cosmetic, dye, polymer resin, rubber, adhesive, sealant, coating, composite material, or laminated or bonded material composition containing, or resulting from a chemical modification of, such anabolic phloroglucinol, or of resorcinol prepared therefrom;

Processes for the preparation of recombinant cells that are capable of biosynthesizing phloroglucinol from malonyl-CoA, involving transforming a cell with such a PhlD-encoding nucleic acid that is capable of expression by the cell, or involving inactivating genes in a phlD+ cell by providing a phlD+ cell that is at least one of phlA+, phlB+, or phlC+, and inactivating at least one of the phlA, phlB, or phlC genes therein; such recombinant cells that are microbes, such as bacteria, examples of which include *Escherichia coli* and *Pseudomonas fluorescens*; such processes in which the enzyme system or recombinant cell comprises a malonyl-CoA synthesis enzyme; such processes involving providing a phlABCD+ cell, and either or both of inactivating at least one phlA, phlB, or phlC gene thereof or inserting at least one phlD+ nucleic acid therein that is at least one of phlA−, phlB−, or phlC−; such processes in which the phlD+ recombinant cell is phlA−, phlB−, and phlC−; such processes involving providing a phlABCD+ cell, and inactivating all of the phlA, phlB, and phlC genes thereof; such processes involving providing a phlABCD− cell and inserting a phlD gene therein; such processes in which the phlD+ nucleic acid is located in genomic DNA of the cell; such processes in which it is located in extra-genomic DNA of the cell.

Methods for producing propellant or explosive compounds involving providing anabolic phloroglucinol biosynthesized by such an isolated or recombinant enzyme system or recombinant cells and chemically modifying the anabolic phloroglucinol, or chemically modifying resorcinol prepared therefrom;

Uses of such anabolic phloroglucinol, or of resorcinol prepared therefrom, in the manufacture of an explosive or propellant; and explosive or propellant compositions containing, or resulting from a chemical modification of, such anabolic phloroglucinol, or of resorcinol prepared therefrom.

Figure 1:
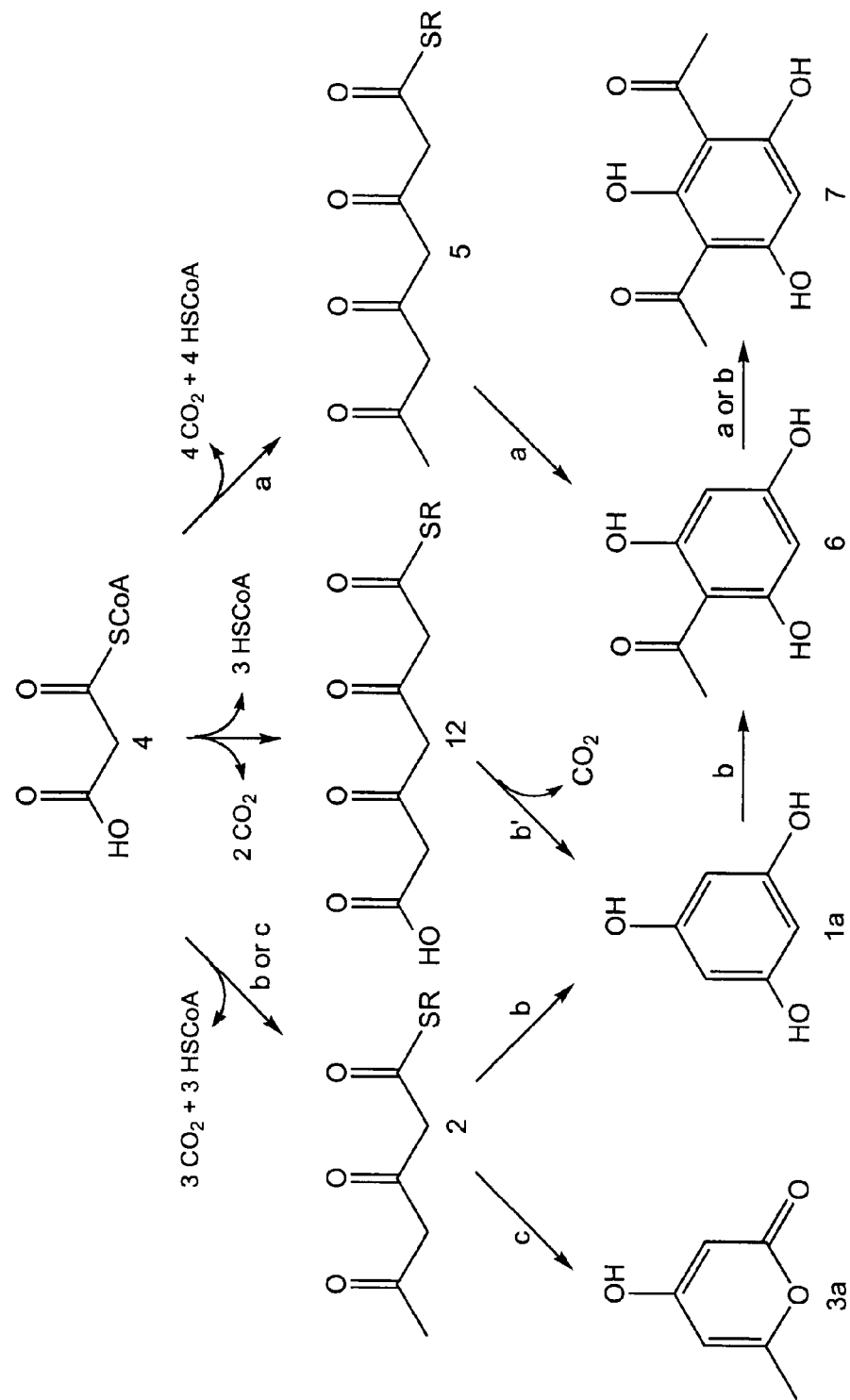
FIG. 1 presents Scheme 1, which illustrates literature-reported routes: (a) for acetylphloroglucinol biosynthesis without phloroglucinol as an intermediate, see M. G. Bangera & L. S. Thomashow, *J Bact.* 181(10):3155-63 (1999); and (c) for triacetic acid lactone biosynthesis, see S. Eckermann et al., *Nature* 396:387 (1998), J. M. Jez et al., *Chem. Bio.* 7:919 (2000); W. Zha et al., *J. Am. Chem. Soc.* 126:4534 (2004). Also shown are the routes (b) and (b') postulated and identified in the present work for acetylphloroglucinol biosynthesis with phloroglucinol as an intermediate.

It should be noted that the figures set forth herein are intended to exemplify the general characteristics of an apparatus, materials and methods among those of this invention, for the purpose of the description of such embodiments herein. These figures may not precisely reflect the characteristics of any given embodiment, and are not necessarily intended to define or limit specific embodiments within the scope of this invention.

DETAILED DESCRIPTION

The present invention provides methods, materials and organisms for producing phloroglucinol and derivatives thereof. The present invention is based on work in which it was surprisingly discovered that, instead of expressing multiple genes involved in the microbial acetylphloroglucinol pathway, e.g., phlABCDEF, expression of a single gene could produce substantial concentrations of phloroglucinol itself Publications, such as U.S. Pat. No. 6,051,383, Thomashow et al., issued Apr. 18, 2000, led to the conclusion that, if phloroglucinol were to be produced by use of such genes, it was a highly likely possibility that the best or only route to do so would be to add at least one more enzyme to the pathway to de-acetylate the acetylphloroglucinols.

Instead, it has now been unexpectedly found that expression of a single enzyme, named herein as "phloroglucinol synthase" and expressed from a phlD gene, results in formation of phloroglucinol directly, i.e. not through an acetylated or diacetylated intermediate. As a result, this one enzyme can be expressed alone, apart from any other phl operon genes, to obtain significant levels of phloroglucinol synthesis. In addition, this route of phloroglucinol synthesis proceeds through a 3,5-diketohexanoate thioester intermediate, not through a 3,5,7-triketooctanoate thioester. It has been further discovered that expression of the phloroglucinol synthase per se, apart from any other phl operon genes, has now been demonstrated to be capable of producing significantly more phloroglucinol than any other biosynthetic or semi-biosynthetic route proposed to date; and that phloroglucinol is thereby produced in a simpler, more efficient and economic manner than any other biosynthetic or semi-biosynthetic route yet proposed.

The headings (such as "Introduction" and "Summary,") and sub-headings used herein are intended only for general organization of topics within the disclosure of the invention, and are not intended to limit the disclosure of the invention or any aspect thereof In particular, subject matter disclosed in the "Introduction" may include aspects of technology within the scope of the invention, and may not constitute a recitation of prior art. Subject matter disclosed in the "Summary" is not an exhaustive or complete disclosure of the entire scope of the invention or any embodiments thereof.

The citation of references herein does not constitute an admission that those references are prior art or have any relevance to the patentability of the invention disclosed herein. Any discussion of the content of references cited in the Introduction is intended merely to provide a general summary of assertions made by the authors of the references, and does not constitute an admission as to the accuracy of the content of such references. All references cited in the Description section of this specification are hereby incorporated by reference in their entirety.

The description and specific examples, while indicating embodiments of the invention, are intended for purposes of illustration only and are not intended to limit the scope of the invention. Moreover, recitation of multiple embodiments having stated features is not intended to exclude other embodiments having additional features, or other embodiments incorporating different combinations the stated of features.

As used herein, the words "preferred" and "preferably" refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, the word "include," and its variants, is intended to be non-limiting, such that recitation of items in a list is not to the exclusion of other like items that may also be useful in the materials, compositions, devices, and methods of this invention.

The word "recombinant" is used herein to indicate that nucleic acid manipulation was employed. As a result, phrases such as "recombinant" nucleic acid, "recombinant" polypeptide, and "recombinant" cell to entities that were produced, at least in part, by nucleic acid manipulation. The term "in vivo" is used herein to include "in cyto" where the cell is a living cell.

Sequence Homology

In a preferred embodiment, a mutant polypeptide according to the present invention will have an amino acid sequence that is at least 50% homologous to that of a native polypeptide performing the same function as the mutant. By way of example, a phloroglucinol synthase according to the present invention will have an amino acid sequence at least 50% homologous to that of SEQ ID NO:2; in a preferred embodiment, the sequence will be at least 60% homologous thereto; in a preferred embodiment, the sequence will be at least 70% homologous thereto; in a preferred embodiment, the sequence will be at least 80% homologous thereto; in a preferred embodiment, the sequence will be at least 90% homologous thereto.

In one embodiment, a recombinant polynucleotide according to the present invention, which encodes a desired polypeptide, will be any that encodes a polypeptide having homology to a native polypeptide of the same function, as described above. In one embodiment, a recombinant polynucleotide according to the present invention, which encodes a desired polypeptide, will have an amino acid sequence that is more than 80% homologous to that of a native polynucleotide encoding a polypeptide performing the same function as the mutant. In a preferred embodiment, the polynucleotide will be at least 85% homologous thereto; in a preferred embodiment, the polynucleotide will be at least 90% homologous thereto; in a preferred embodiment, the polynucleotide will be at least 95% homologous thereto.

Sequence homology refers to the degree of identicality between two sequences of amino acid residues, or between two sequences of nucleobases. This may be determined by visual comparison of two sequences, or by use of bioinformatic algorithms that align sequences for comparison or that determine percent homology among compared sequences. Useful automated algorithms are available in the GAP, BEST-FIT, FASTA, and TFASTA computer software modules of the Wisconsin Genetics Software Package (available from Genetics Computer Group, Madison, Wis., USA). The alignment algorithms automated in those modules include the Needleman & Wunsch, the Pearson & Lipman, and the Smith & Waterman sequence alignment algorithms. Other useful algorithms for sequence alignment and homology determination are automated in software including: FASTP, BLAST, BLAST2, PSIBLAST, and CLUSTAL V; see, e.g., N. P. Brown et al., Bioinformatics: Applications Note, 1998, 14:380-81; the U.S. National Center for Biotechnology Information; and U.S. Pat. No. 6,790,639, Brown et al., issued Sep. 14, 2004, which provides software parameter settings useful for homology determination herein.

The sequence homology exhibited by nucleobase polymers, such as nucleic acids and nucleic acid analogs, may be determined by hybridization assays between a first sequence and the complement of a second sequence. Any of the well known hybridization assays may be used for this purpose, and examples of these include those described in U.S. Pat. No. 6,767,744, Koffas et al., issued Jul. 27, 2004, and U.S. Pat. No. 6,783,758, Wands et al., issued Aug. 31, 2004, with "high stringency" hybridization conditions being as defined therein.

Conservative Substitutions

In addition, conservative amino acid substitutions may be present in a polypeptide according to the present invention. The term "conservative amino acid substitution" indicates any amino acid substitution for a given amino acid residue, where the substitute residue is so chemically similar to that of the given residue that no substantial decrease in polypeptide function (e.g., enzymatic activity) results. Conservative amino acid substitutions are commonly known in the art and examples thereof are described, e.g., in U.S. Pat. No. 6,790,639, Brown et al., issued Sep. 14, 2004; U.S. Pat. No. 6,774,107, Strittmatter et al., issued Aug. 10, 2004; U.S. Pat. No. 6,194,167, Browse et al., issued Feb. 27, 2001; or U.S. Pat. No. 5,350,576, Payne et al, issued Sep. 27, 1994. In a preferred embodiment, a conservative amino acid substitution will be any one that occurs within one of the following six groups 1. Small aliphatic, substantially non-polar residues: Ala, Gly, Pro, Ser, and Thr;
2. Large aliphatic, non-polar residues: Ile, Leu, and Val; Met;
3. Polar, negatively charged residues and their amides: Asp and Glu;
4. Amides of polar, negatively charged residues: Asn and Gln; His;
5. Polar, positively charged residues: Arg and Lys; His; and
6. Large aromatic residues: Trp and Tyr; Phe.

In a preferred embodiment, a conservative amino acid substitution will be any one of the following, which are listed as Native Residue (Conservative Substitutions) pairs: Ala (Ser); Arg (Lys); Asn (Gln; His); Asp (Glu); Gln (Asn); Glu (Asp); Gly (Pro); His (Asn; Gln); Ile (Leu; Val); Leu (Ile; Val); Lys (Arg; Gln; Glu); Met (Leu; Ile); Phe (Met; Leu; Tyr); Ser (Thr); Thr (Ser); Trp (Tyr); Tyr (Trp; Phe); and Val (Ile; Leu).

Just as a polypeptide may contain conservative amino acid substitution(s), a polynucleotide hereof may contain conservative codon substitution(s). A codon substitution is considered conservative if, when expressed, it produces a conservative amino acid substitution, as described above. Degenerate codon substitution, which results in no amino acid substitution, is also useful in polynucleotides according to the present invention. Thus, e.g., a polynucleotide encoding a selected polypeptide useful in an embodiment of the present invention may be mutated by degenerate codon substitution in order to approximate the codon usage frequency exhibited by an expression host cell to be transformed therewith, or to otherwise improve the expression thereof.

Moreover, nucleobase sequence-containing polymers, such as nucleic acids, will preferably include those encoding an enzyme or enzymes according to the present invention. In addition, these will include, e.g., nucleic acids sharing at least 80% sequence homology with a given enzyme-encoding nucleic acid. By way of example, a phloroglucinol synthase coding sequence according to the present invention will have a base sequence at least 80% homologous to that of SEQ 1D NO:1; in a preferred embodiment, the sequence will be at least 85% homologous thereto; in a preferred embodiment, the sequence will be at least 90% homologous thereto; in a preferred embodiment, the sequence will be at least 95% homologous thereto.

Production of Phloroglucinol and its Derivatives

Figure 3:
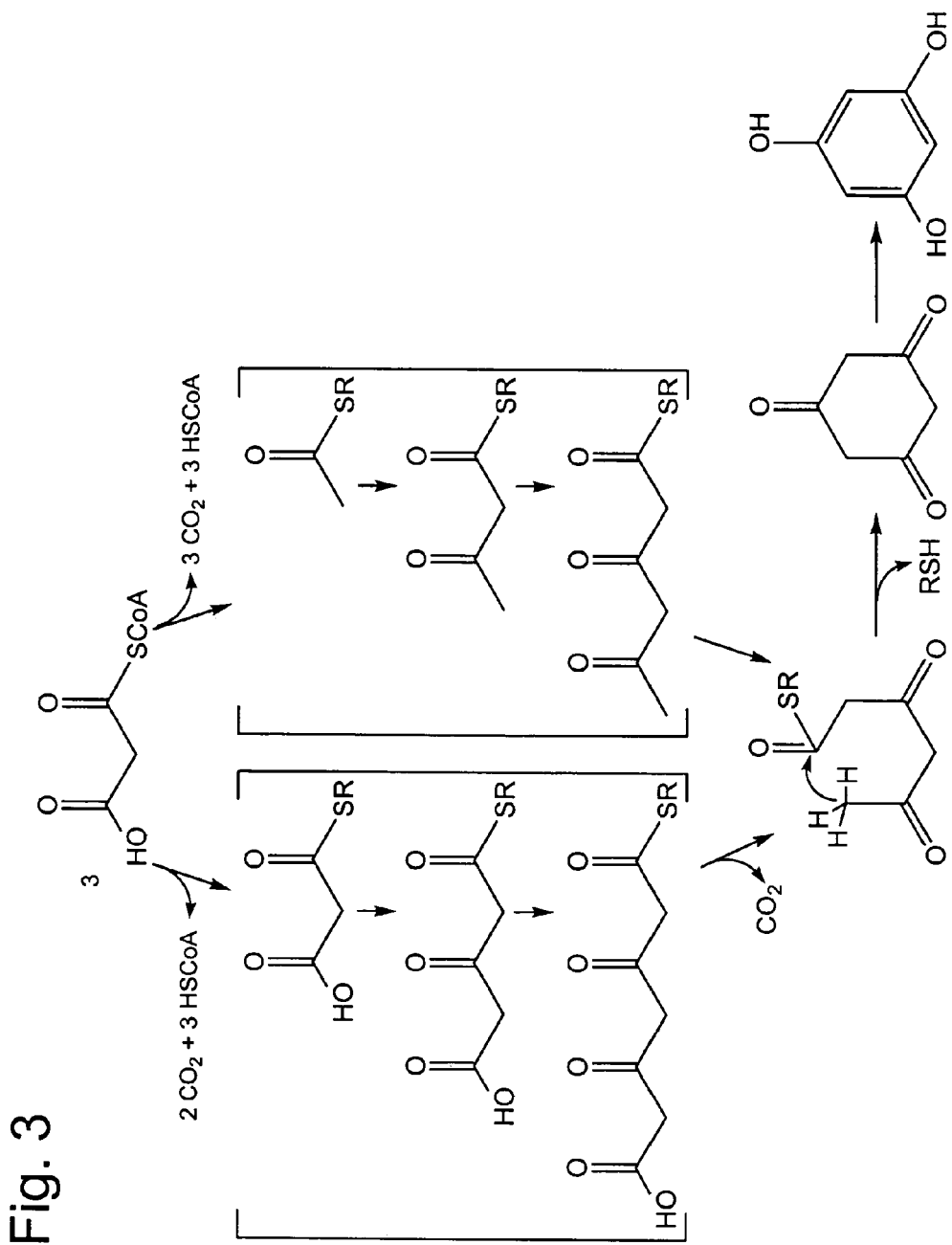
FIG. 3 presents putative reaction pathways according to the present invention, by which malonyl-CoA is biosynthetically converted to phloroglucinol by a phloroglucinol synthase, either via enzyme-activated 3,5-diketopimelate (3,5-diketoheptanedioate) or via enzyme-activated 3,5-diketohexanoate (3,5-diketocaproate).

As illustrated in FIG. 3, a phloroglucinol synthase has now been identified and characterized, and the mechanism by which this enzyme catalyzes phloroglucinol synthesis has been unexpectedly found to proceed according to the following series of steps, or via an alternative mechanism in which the first malonyl-CoA providing the group that is transferred to form the illustrated thioester (—SR) linkage, provides a malonyl, rather than an acetyl group, therefor.

Acetyl Activation—The first step involves activation of an acetyl group. This occurs by decarboxylation of malonyl-CoA to transfer an acetyl group therefrom to the enzyme, thus forming an enzyme-activated acetyl thioester ("R" in FIG. 3 represents the enzyme or a moiety attached thereto); in an alternate embodiment, the first step involves activation of an entire malonyl group to faun an enzyme-activated malonyl thioester;

Chain Extension—The next phase involves two successive malonyl-CoA decarboxylations to transfer further acetyl groups to form an enzyme-activated 3-ketobutanoate thioester and then an enzyme-activated 3,5-diketohexanoate thioester; in an alternate embodiment, successive transfers form enzyme-activated: 3-ketoglutarate thioester and 3,5-diketopimelate thioester;

Cyclization—The final step involves cyclization of the 3,5-diketohexanoate thioester intermediate to form phloroglucinol; in an alternative embodiment, a decarboxylation of 3,5-diketopimelate takes place to permit cyclization to phloroglucinol.

All three steps are catalyzed by phloroglucinol synthase.

An enzyme system according to the present invention will contain at least one phloroglucinol synthase. In a preferred embodiment, the phloroglucinol synthase will be obtained from a Pseudomonad; in a preferred embodiment it will be obtained from a member of the genus *Pseudomonas*; in a preferred embodiment, it will be obtained from a member of the species *P. fluorescens*. In a preferred embodiment, it will be obtained from *P. fluorescens* Pf-5. The amino acid sequence of the *P. fluorescens* Pf-5 phloroglucinol synthase identified in the present work is shown in SEQ ID NO:2, and its native coding sequence is shown in SEQ ID NO:1.

In a preferred embodiment, an enzyme system according to the present invention will further contain at least one enzyme capable, either solely or jointly with other enzyme(s), of catalyzing the formation of malonyl-CoA. Malonyl-CoA may be biosynthetically produced, e.g., from acetyl-CoA by a malonyl-CoA synthesis enzyme, such as: the malonyl-CoA synthetase (MatB) from *Rhizobium leguminosarum* (see GenBank Accession AAC83455 [gi:3982573]), which converts malonate to malonyl-CoA; the malonyl-CoA decarboxylase (MatA) from *Rhizobium leguminosarum* (see GenBank Accession AAC83456 [gi:3982574]), which converts malonic semialdehyde to malonyl-CoA; or the transcarboxylase activity of acetyl-CoA carboxylase (EC 6.4.1.2), which carboxylates acetyl-CoA to form malonyl-CoA. The malonic acid, malonic semialdehyde, or acetyl-CoA starting material may be, and preferably is, biosynthetic; for example, the acetyl-CoA may have been biosynthetically derived from any one of a variety of sources, such as glucose, photosynthetic 3-phosphoglycerate, etc.

An enzyme system according to the present invention can be either in vitro or in vivo. Where a malonyl-CoA synthesis enzyme is not provided, malonyl-CoA will be supplied to the medium in contact with the cells and/or enzymes. In one embodiment, a phloroglucinol synthase-encoding nucleic acid may be transformed into cells of an organism capable of synthesizing malonyl CoA, in which case phloroglucinol may be produced therein. Examples of organisms synthesizing malonyl CoA include plants, algae, animals, and humans. In vitro systems include, e.g., batch enzyme suspensions or (adsorbed or covalently) immobilized enzyme bioreactors. In vivo systems include, e.g., immobilized cell bioreactors, continuous fermentations, and batch fermentations. "Fermentation" as used herein indicates cultured cell growth under any effective conditions, rather than a requirement for, e.g., anaerobic conditions or anaerobic metabolism, which is merely permitted as another embodiment hereof. In any embodiment, a source of malonyl-CoA will be provided to the phloroglucinol synthase, whether or not that source is added (e.g., exogenous) malonyl-CoA or in situ biosynthesized (e.g., endogenous) malonyl-CoA.

Recombinant cells according to the present invention are capable of expressing at least one phloroglucinol synthase and optionally at least one malonyl-CoA synthesis enzyme, but neither an entire phlABCD operon nor all three of phlA, phlB, and phlC genes. In a preferred embodiment, a recombinant cell will be one that is capable of expressing a recombinant phloroglucinol synthase therein. In a preferred embodiment, the recombinant cell capable of expressing phloroglucinol synthase and optionally of expressing a malonyl-CoA synthesis enzyme, will be a walled cell. Examples of walled cells include plant cells, yeast/fungal cells, bacterial cells, Archaea cells, and some protists. In one embodiment, the recombinant cell will be an avascular plant (e.g., moss), protist (e.g., algae), yeast, fungal, bacterial, or archaeal cell. In one embodiment, the recombinant cell will be a recombinant microbe. In one embodiment, the recombinant cell will be a yeast, fungal, bacterial, or archaeal cell, more preferably a yeast, fungal, or bacterial cell. In a preferred embodiment, the recombinant cell will be a bacterial cell. In a preferred embodiment, the recombinant cell will be a proteobacterial cell. Preferably, the recombinant cell will lack the ability to express functional enzymes from phlABC, phlE, and phlF genes. In a preferred embodiment, the cell will be a phlABC$^-$, phlE$^-$, and phlF$^-$ cell. Recombinant host cells will contain at least one nucleic acid encoding a phloroglucinol synthase according to the present invention. In a preferred embodiment, the nucleic acid will be in the form of a vector, such as a plasmid or transposon.

In one embodiment for forming a useful phlD$^+$ recombinant cell hereof, a cell that is both phlD$^+$ and phlA$^+$, phlB$^+$, and/or phlC$^+$ will be made phlA$^-$, phlB$^-$, and/or phlC$^-$, as by any gene knockout technique (i.e. any gene excision or mutation technique that results in the cell's inability to make the functioning expression product encoded by the pre-knocked-out gene). Preferably, all of the phlA, phlB, and phlC genes present in the cell will be knocked out. The resulting cell will retain its phlD$^+$ phenotype. Optionally, phlE and/or phlF genes present in the cell may also be knocked out. In one preferred embodiment, a phlABCD$^+$ cell will be made phlABC$^-$. In one embodiment, a cell that is both phlD$^-$ and phlA$^-$, phlB$^-$, and/or phlC$^-$ will be made phlD$^+$ by inserting an expressible PhlD-encoding nucleic acid into the cell, whether into the genomic DNA thereof or as part of an extrachromosomal unit, such as a plasmid, or both. In one preferred embodiment, a phlABCD$^-$ cell will be made phlD$^+$.

In some embodiments, a native or recombinant cell that is PhlD$^+$, such as a phlD$^+$ cell, can be further supplemented with additional phlD gene(s), as by transformation with nucleic acid comprising one or more expressible open reading frames encoding a phloroglucinol synthase. The PhlD$^+$ cell may be a PhlA$^-$, PhlB$^-$, and/or PhlC$^-$ cell, such as a phlA$^-$, phlB$^-$, and/or phlC$^-$, or it may be a PhlA$^+$, PhlB$^+$, and/or PhlC$^+$ cell, such as a phlA$^+$, phlB$^+$, and/or phlC$^+$ cell (e.g., a phlABCD$^+$ cell). The resulting recombinant cell, which is capable of expressing the additional phlD gene(s) can exhibit enhanced phloroglucinol synthesis capability.

Similarly to recombinant cells, isolated or recombinant enzyme systems according to the present invention comprise at least one phloroglucinol synthase, and optionally at least one malonyl-CoA synthesis enzyme or enzyme set, but do not comprise all three of PhlA, PhlB, and PhlC enzymes, and preferably comprise none of PhlA, PhlB, and PhlC enzymes. Thus, recombinant cells and enzyme systems according to the present invention, which comprise at least one phloroglucinol synthase and optionally at least one malonyl-CoA synthesis enzyme, but do comprise fewer than all three of PhlA, PhlB, and PhlC enzymes, can both be referred to as PhlD+ entities that are at least one of PhlA−, PhlB−, and PhlC−, and preferably are PhlABC−.

Processes for the production of phloroglucinol involve contacting a phloroglucinol synthase with malonyl-CoA. Processes for the production of resorcinol involve performing a hydrogenation reaction upon biosynthetic phloroglucinol, e.g., using hydrogen and a rhodium catalyst. Phloroglucinol and resorcinol produced by a process according to the present invention may be used in or as, or to prepare, compositions such as medicaments, cosmetics, dyes, polymer resins, rubbers, adhesives, sealants, coatings, propellants, explosives, composite materials, and laminated or bonded materials.

Whole-Cell Fermentation Modes

Whole cell fermentations of recombinant cells hereof may be performed in any culture mode, preferably in a batch, fed-batch, or continuous (or semi-continuous, i.e. reseeding) mode. In some embodiments hereof, phloroglucinol-containing spent medium produced by a culture of recombinant cells according to the present invention is processed to extract phloroglucinol. However, in some cases, phloroglucinol itself, when it reaches a threshold concentration in the growth medium, can exert toxicity against the cultured cells in a process called end-product inhibition. Where present, this inhibition decreases cellular production of phloroglucinol and can result in reduced cell viability. Thus, in some embodiments, an extraction of phloroglucinol, and optionally phloroglucinol derivatives (if present), from an otherwise still-useful growth medium is preferably performed during the period in which the cells are actively producing phloroglucinol. Such an embodiment is referred to herein as an "extractive fermentation."

Extractive fermentation can be performed herein in any of the modes known useful in the art. For example, some embodiments employ a dispersed extractive fermentation mode in which an extractive absorbent or adsorbent liquid or particle phase, which is capable of uptaking phloroglucinol, is introduced into the medium in which the recombinant cells are grown, where the extractive particles or liquid zones come into contact with and uptake phloroglucinol. As in any extractive process, uptake of this product by the absorbent or adsorbent material can be non-specific, preferential, or specific, and is preferably preferential or specific for phloroglucinol.

After becoming "loaded" with phloroglucinol, the "loaded" extractive phase is removed from the culture medium, e.g., by centrifugation, filtration, magnetic collection of magnetic or magnetizable particles, and/or by phase separation such as where the extractive phase rises above or sinks below the bulk of the culture medium. In some embodiments, a counter-current or cross-current extraction technique may be utilized to extract phloroglucinol from the culture medium, such as where the stream that is counter-current or cross-current to the culture medium stream comprises such an extractive liquid or particle phase.

In some embodiments, a membrane extractive fermentation is performed by passing the culture medium over an extraction membrane, such as an ion exchange membrane. In some embodiments, a column extractive fermentation is performed by passing the culture medium through an extraction column, such as a hollow fiber membrane extractor or a fibrous or bead resin column. The cells in culture in the medium may pass through the column, or some or all of the cells may be removed, e.g., by filtration, before the medium is passed through the column. In any extractive fermentation process, the extractive fermentation can be performed once, multiple times, or continuously during the fermentation process. In counter-current, cross-current, membrane, and column extractive fermentation modes, the medium from which some or all (preferably most or all) of the phloroglucinol has been removed, is then returned to the fermentation vessel.

In a preferred embodiment, a column extractive fermentation technique is employed to remove phloroglucinol from the culture medium during biosynthesis. Useful media for this purpose include anion exchange media, such as anion exchange beads, fibers, and hollow fibers. Anion exchange membranes and anion exchange media particles are likewise useful in membrane and dispersed extractive fermentation modes, respectively. Where a particulate anion exchange medium is used, it will preferably be utilized in a fluidized bed extractive fermentation mode, although stationary bed modes may alternatively be used.

Useful anion exchange media may comprise any support, whether organic or inorganic, that contains or is covalently attached to anion exchange groups. In some embodiments, an organic support will be used, such as a styrene-divinylbenzene, polystyrene, polyvinyl, acrylic, phenol-formaldehyde, organosilicon, or cellulose polymer backbone, wherein the backbone comprises or is attached to anion exchange groups.

Useful anion exchange groups may be any cationic group, preferably non-metal cationic groups, such as organic ammonium, sulfonium, and phosphonium groups. Preferred cationic groups include organic: tertiary ammonium (e.g., diethylaminoethyl cellulose), quaternary ammonium, pyridinium, tertiary sulfonium, and quaternary phosphonium groups. In one embodiment, the anion exchange groups of the anion exchange medium will be quaternary ammonium or pyridinium groups. Examples of quaternary ammonium-type resins include AG-1 X8 resin (from Bio-Rad Laboratories Inc., Hercules, Calif., USA) and DOWEX 1 resin (from The Dow Chemical Co., Midland, Mich., USA); examples of pyridinium-type resins include polyvinyl-alkyl-pyridinium resins obtainable by alkyl halide treatment of polyvinyl-pyridine resins, such as REILLEX HP (from Reilly Industries, Inc., Indianapolis, Ind., USA), or obtained directly from commercial sources, such as poly(4-vinyl N-methyl pyridinium iodide) (from Polymer Source Inc., Montreal, QC, Calif.).

In one preferred embodiment, the anion exchange medium will be treated to prepare a phosphate complex with cationic groups of the medium, prior to use. Where an anion exchange medium is re-used (without intervening removal of phloroglucinol therefrom), or is in continuous contact, with a given fermentation, it will preferably be replaced with new or renewed anion exchange medium frequently enough that the phloroglucinol concentration of the culture medium does not rise to a level at which a substantial degree of end-product-inhibition would occur; preferably not above about 2 g/L, or not above about 1.5 g/L, phloroglucinol.

Anion exchange medium that has already been loaded with phloroglucinol, by either an extractive fermentation or a post-fermentation extraction process, is preferably treated to removal phloroglucinol by washing it with water, acidified water, acidified alcohol (e.g., acidic ethanol) or a combination thereof. Water washing followed by acidified alcohol washing is one preferred technique. After (preferably) most or all of the phloroglucinol has been removed from the anion exchange medium, that medium can be prepared for re-use in phloroglucinol extraction, e.g., by equilibrating it with a phosphate solution to form cationic group-phosphate complexes prior to re-use. Phloroglucinol present in the washes may be further isolated and/or purified by any techniques known in the art, e.g., phase separation, solvent evaporation, and so forth.

Whole-Cell Fermentation Conditions

A culture of whole cells used in a method for producing phloroglucinol according to the present invention will utilize conditions that are permissive for cell growth and those that permit the cultured cells to produce anabolic phloroglucinol. In some cases, a phloroglucinol synthase will be expressed throughout the cell culture period, e.g., constitutively; yet, in many cases, it is desirable to begin expressing phloroglucinol synthase only near the end of the exponential growth phase (EGP). Where a later expression is desired, a phloroglucinol synthase coding sequence that is under the control of a regulated promoter generally will be activated or derepressed when about 70 to 100%, preferably when about 70 to about 90%, more preferably when about 70 to about 80% of EGP has elapsed. Examples of promoters useful for this purpose include the tac, T5, and T7 promoters; $P_{T7}$ is preferred among these; induction may be made using lactose or a gratuitous inducer such as IPTG (isopropyl-beta-D-thiogalactopyranoside).

In some preferred embodiments hereof, a recombinant microbial cell, such as a recombinant bacterial host cell will be used as a whole cell biocatalyst herein. Preferred bacteria for this purpose include proteobacteria; preferred examples of proteobacteria include the gamma proteobacteria, such as enterobacteria and pseudomonads; Escherichia spp., such as E. coli, and Pseudomonas spp., such as P. fluorescens, are preferred among these. Preferred microbes are those that lack or have been treated to decrease or eliminate protease activities that would be capable of degrading the phloroglucinol synthase and/or malonyl-CoA synthesis enzymes according to the present invention. In bacteria, Lon and OmpT are two proteases that are preferably absent or are otherwise decrease or eliminated, e.g., by mutation. E. coli strains BL21 and W3110 are preferred examples of phlABCD$^-$ cells for insertion of phlD gene(s); and P. fluorescens strain Pf-5 is a preferred example of phlABCD$^+$ cells for inactivation of phlA, phlB, and/or phlC, with or without insertion of further phlD gene(s), or for inactivation of phlABCD, with insertion of further phlD gene(s), or for supplementation with additional phlD gene(s). E. coli strain BL21 may be obtained as: BL21 STAR (DE3) ONE SHOT (Invitrogen Corp., Carlsbad, Calif., USA); or ULTRA BL21 (DE3) (Edge BioSystems, Gaithersburg, Md., USA). E. coli strain W3110 may be obtained as ATCC No. 27325 (American Type Culture Collection, Manassas, Va., USA); and P. fluorescens strain Pf-5 may be obtained as ATCC No. BAA-477.

In the case of E. coli, preferred fermentation temperatures are from about 20 to about 37° C., preferably about 25 to about 37° C., more preferably about 30 to about 37° C. It has been discovered that, in the case of anabolic phloroglucinol synthesis, a combination of a higher temperature during EGP, or at least during the pre-induction portion of EGP, and a lower temperature during at least part of the remaining culture period (e.g., throughout all or part of the post-induction or all or part of the maintenance phase), is an important feature of a superior phloroglucinol production protocol. Thus, in one preferred embodiment, recombinant E. coli cells will be grown at about 35-37° C., preferably at about 36-37° C., more preferably at about 36° C. during EGP, or during pre-induced EGP; and at about 30-34° C., preferably at about 30 to about 33° C., more preferably at about 33° C. or about 30° C. during maintenance phase, or during post-induction. In some embodiments, the switch to a lower temperature may occur well into the maintenance phase, e.g., up to about 15 hours after EGP has ended. Thus, in the case of a cell (e.g., E. coil) culture in which EGR ends at about 15 hours from the start of culturing, the switch from a higher to a lower temperature for a two-temperature fermentation profile may occur, e.g., at about 11 or about 12 hours (e.g., at approximately the same time as a 70% or 80% EGR induction point), or at about 15 hours, or even up to about 30 hours from the start of culturing. Alternatively, the higher temperatures useful, e.g., for EGR in such a dual-temperature embodiment are useful temperatures for the entire culturing period. In the case of P. fluorescens, preferred temperatures are from about 20 to about 30° C., with preferred higher temperatures being from about 27 to about 30° C., and preferred lower temperatures being from about 24 to about 27° C.

Carbon Sources

Figure 4:
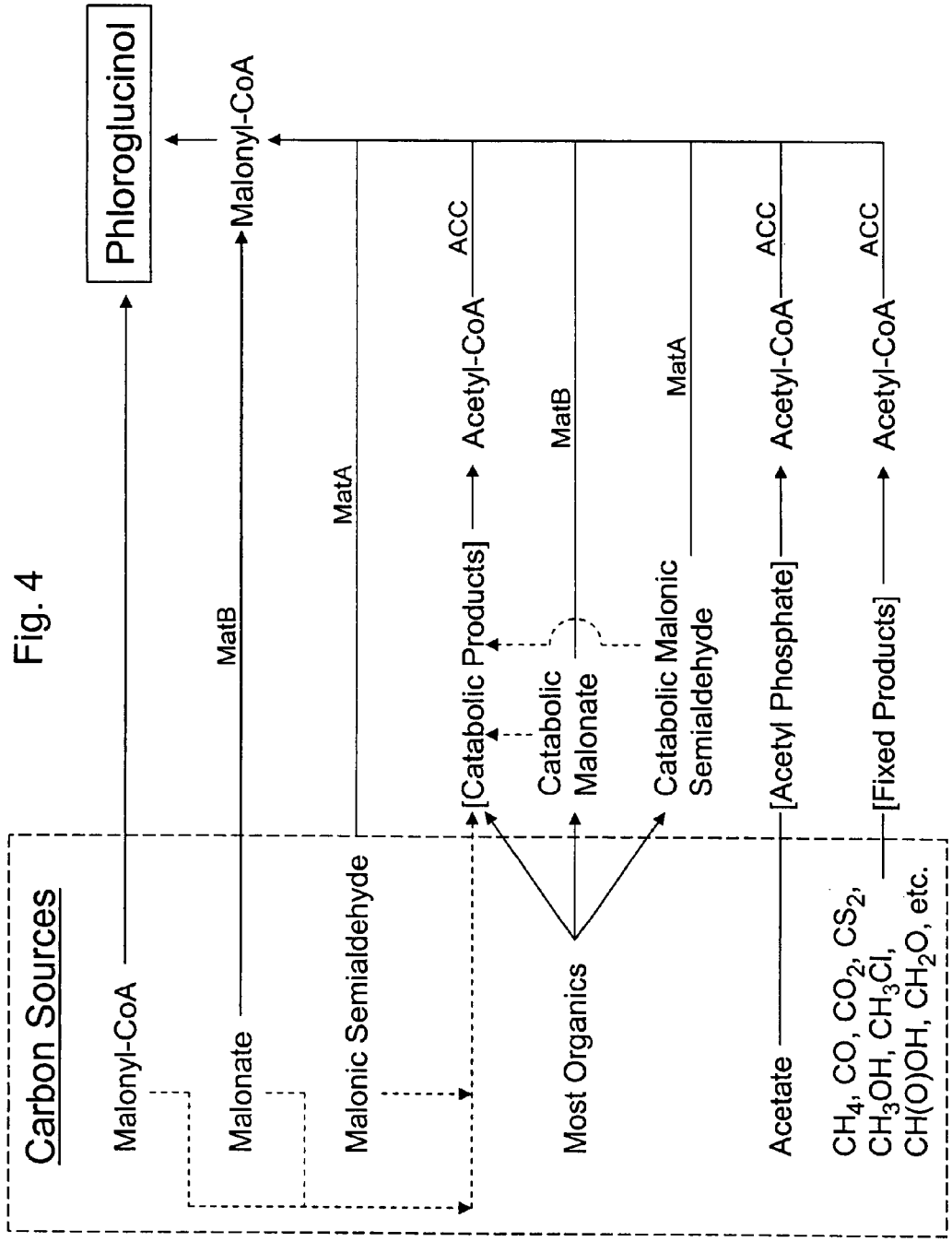
FIG. 4 illustrates a variety of exemplary pathways for utilization of different carbon sources in a process for anabolic phloroglucinol synthesis. Dashed arrows show possible alternative carbon source utilization routes; square brackets enclose intermediates that may be absent in some pathways.

Cells, enzyme systems, and methods for producing phloroglucinol according to embodiments of the present invention will utilize a carbon source. Where a carbon source other than malonyl-CoA is contacted with the cell or enzyme system, an enzyme system or recombinant cell according to the present invention can utilize any other carbon source, provided that the enzyme system or recombinant cell according to the practiced embodiment can metabolize the carbon source into substances that can be used to anabolically synthesize phloroglucinol as described herein. The nature of the other enzymology, besides the phloroglucinol synthase, and the optional malonyl-CoA synthesis activity, present in the reaction mixture will determine which carbon sources may be used. FIG. 4 illustrates a number of representative routes for anabolic synthesis of phloroglucinol from carbon sources.

Thus, in the case of most carbon sources, the cell or enzyme system will first either catabolize the carbon source or will fix it, in order to provide simple organic molecules from which the cell may form acetyl-CoA. Alternatively, the carbon source will be directly converted to acetyl-CoA. For example, in the case of an acetate carbon source, the acetate can be directly converted to acetyl-CoA, or it may first be converted to acetyl phosphate. Acetyl-CoA may itself be used as a carbon source. Once obtained or provided, the acetyl-CoA can then be used in the synthesis of malonyl-CoA, as by action of acetyl-CoA carboxylase. Where degradation of a carbon source produces catabolic malonate or catabolic malonic semialdehyde, or where malonate or malonic semialdehyde is present in the carbon source, these may be converted to malonyl-CoA by a malonyl-CoA synthetase or malonyl-CoA decarboxylase, respectively, present in the enzyme pool of the cell or enzyme system, or they may be catabolized for use in acetyl-CoA synthesis, with subsequent conversion to malonyl-CoA. Once obtained or provided, malonyl-CoA is then used as a substrate by phloroglucinol synthase, forming phloroglucinol Where the carbon source comprises a biomolecule-type carbon compound, the carbon compound will preferably be a primary metabolite-type compound. Examples of primary metabolite-type compounds include any of the, preferably C1-C18: fatty acids, waxes, mono-, di-, and tri-glycerides; polyols; aliphatic hydroxy acids; phospholipids; phosphoacids; monosaccharides (e.g., trioses, tetroses, pentoses, hexoses, heptoses, and the like); amino acids; and nucleotides; and hydrolysable homo- and hetero-oligomers (i.e., including -dimers) and -polymers formed from such compounds; and biologically activated forms of such compounds (e.g., acetyl-CoA). Biomolecule-type compounds may be of any origin, whether biological or synthetic. Other preferred compounds include any small or non-complex organic compounds, i.e. generally C1-C18, aliphatic cycloaliphatic, and aromatic compounds, and the like, of any source, having a preferred monomeric complexity of 4 or fewer carbon-carbon branch points per 18 carbon atoms, e.g.: C1-C18 aliphatic hydrocarbons and their mono- and poly-acids, -alcohols, -amines, -carbonyls; and hydrolysable homo- and hetero-oligomers and -polymers formed therefrom.

Carbon sources comprising such small/non-complex organic(s), and/or primary metabolite-type compound(s), without substantial concentrations of (and preferably less than 10%-of-carbon-by-weight concentrations of) secondary metabolites or of larger-monomer-type or complex organic compounds are also referred to herein as "simple" carbon sources. As used herein, secondary metabolites include, e.g.: alkaloids; coumarins; polyketides; terpenoids, isoprenoids, sterols, steroids, and prostaglandins; catecholamines; porphyrins; xanthones; flavonoids; phenylpropanoids and phenolics (including, e.g., benzenoids and polyphenolics); and the like. Large or complex organic compounds are aliphatic, cycloaliphatic, and aromatic compounds, and the like, that have a monomeric compound size above C18 and/or a monomeric compound complexity above 4 carbon-carbon branch points per 18 carbon atoms.

In a preferred embodiment, a carbon source will be a simple carbon source. Preferred simple carbon sources contain from 0% to about 5%, more preferably from 0% to about 2%, or 0% to about 1%, or 0% to about 0.5%, or preferably about 0% by weight secondary metabolites and larger or complex organics; or preferably free or at least substantially free of secondary metabolites and larger/complex organics. In some embodiments, a simple carbon source will comprise primary metabolite-type compound(s). Preferred examples of primary metabolite-type compound(s) for use herein include: saccharides, preferably mono- and/or di-saccharides; and polyols. Glucose, xylose, and arabinose are preferred examples of a monosaccharide for use in a carbon source herein; glycerol is one preferred example of a polyol therefore. In one embodiment hereof, glucose, xylose, and/or arabinose will be used as the carbon source, preferably as the carbon source throughout both the exponential growth phase and the maintenance phase of the cell culture. In one embodiment a combination of a monosaccharide(s) (preferably glucose, xylose, and/or arabinose) and glycerol will be used, e.g., a 1:1 or 2:1 weight ratio; preferably, such a combination will be used only during the maintenance phase, with a monosaccharide(s) (without glycerol) being used during the exponential growth phase.

EXAMPLES

Phloroglucinol (1a, Scheme 1, i.e. FIG. 1) is found as a substituent in a variety of natural products. However, biosynthesis of phloroglucinol 1a as a free-standing molecule has not been delineated. As part of a search for such biosynthetic activity, formation of acetylated phloroglucinols (6 and 7, Scheme 1) in *Pseudomonas fluorescens* Pf-5 is examined. B. Novak-Thompson et al., *Can. J. Microbiol.* 40:1064 (1994). Phloroglucinol biosynthesis is detected. Subsequent heterologous expression of *P. fluorescens* phlD leads to accumulation of phloroglucinol 1a in *Escherichia coli* cultures. Beyond the implications relevant to the biosynthesis of acetylphloroglucinols, these discoveries establish the basis for new, environmentally-benign syntheses of phloroglucinol and resorcinol.

Activated 3,5-diketohexanoate 2 (i.e. activated 3,5-diketocaproate) would be a likely precursor to phloroglucinol 1a and triacetic acid lactone 3a (Scheme 1), which are two of the structurally simplest polyketide natural products. For example, 2-pyrone synthase from *Gerbera hybrida* catalyzes the conversion of malonyl-CoA into triacetic acid lactone. S. Eckermann et al., *Nature* 396:387 (1998); J. Jez et al., *Chem. Bio.* 7:919 (2000). Alteration of an active site tyrosine to a phenylalanine results in formation of triacetic acid lactone as the exclusive biosynthetic product in *Brevibacterium ammoniagenes* fatty acid synthase B. W. Zha et al., *J. Am. Chem, Soc.* 126:4534 (2004). Phloroglucinol formation is not observed with any of these naturally-occurring or mutant enzymes. Another, alternative possible precursor to phloroglucinol 1a is activated 3,5-diketo-n-heptanedioate 12. (i.e. activated 3,5-diketopimelate).

Prospecting for the biosynthesis of phloroglucinol 1a leads to *P. fluorescens* Pf-5 and biosynthesis of 2,4-diacetylphloroglucinol 7 (Scheme 1). B. Novak-Thompson et al., *Can. J. Microbial.* 40:1064 (1994). Acetylphloroglucinol biosynthesis is encoded by a gene cluster consisting of phlACBD, a protein for product export encoded by phlE, and a divergently transcribed phlF-encoded regulator. PhlD been suggested to be involved in the formation and cyclization of an activated 3,5,7-triketooctanoate 5 (Scheme 2). The resulting intermediate 2-acetylphroglucinol 6 is then presumably acetylated to from 2,4-diacetylphloroglucinol 7 (Scheme 2). See M. G. Bangera & L. S. Thomashow, *J. Bacteriol.* 181:3155 (1999). Biosynthesis of phloroglucinol 1a is not an activity that has been assigned to PhlD.

*P. fluorescens* Pf-5/pME6031 is examined for products that accumulate in its culture supernatants. In addition (entry 1, Table 1) to accumulation of 2,4-diacetylphloroglucinol 7 and 2-acetylphloroglucinol 6, formation of phloroglucinol is discovered. To increase the concentration of biosynthesized phloroglucinols, *P. fluorescens* PF-5 is transformed with pJA2.232, a plasmid derived from the insertion of the phlAB-CDE gene cluster into pME6031. The goal is to evade regulation by genomically-encoded PhlF by presenting multiple copies of the biosynthetic gene cluster. This approach results in large increases in the concentrations of phloroglucinols 1a, 6, 7 synthesized by *P. fluorescens* Pf-5/pJA2.232 (entry 2, Table 1) relative to *P. fluorescens* Pf-5/pME6031 (entry 1, Table 1).

TABLE 1

Maximum Concentrations of Phloroglucinol 1a, 2-Acetylphloroglucinol 6, and 2,6-Diacetylphlorogluinol 7 Biosynthesized by Constructs Expressing phlACBDE Genes.

| entry | Host/ plasmid | plasmid inserts | phloroglucinols (mg/L) | | |
|---|---|---|---|---|---|
| | | | 1a | 6 | 7 |
| 1 | *P. fluorescens* Pf-5/ pME6031[a] | (none) | 10 | 23 | 35 |
| 2 | *P. fluorescens* Pf-5/ pJA2.232[a] | phlACBDE | 470 | 500 | 790 |
| 3 | *E. coli* BL21(DE3)/ pJA3.085[b] | phlACBDE | 32 | 14 | 0 |
| 4 | *E. coli* BL21(DE3)/ pJA3.156[b] | phlACBD | 22 | 13 | 0 |
| 5 | *E. coli* BL21(DE3)/ pJA2.042[b] | phlD | 720 | 0 | 0 |
| 6 | *E. coli* JWF1(DE3)/ pJA3.131A[c] | phlD | 780 | 0 | 0 |
| 7 | *E. coli* BL21(DE3)/ pJA3.169[b] | phlACB | 0 | 0 | 0 |
| 8 | *E. coli* BL21(DE3)/ pJA3.169[b,d] | phlACB | 39 | 17 | 2 |

[a]Cells are cultured in YM medium under shake-flask conditions.
[b]Cells are cultured under shake-flask conditions in TB medium and harvested. Following resuspension in M9 minimal salts medium, cells are cultured under shake-flask conditions.
[c]Cells are cultured in M9 minimal salts medium under fermentor-controlled conditions.
[d]Phloroglucinol (50 mg/L) added after cells are resuspended in M9 minimal salts.

Further analysis follows from heterologous expression from a T7 promoter of phlACBDE genes in *Escherichia coil* (entries 3-8, Table 1). All *E. coli* constructs also carry a chromosomal gene1 insert encoding the T7 RNA polymerase. *E. coli* Bl21(DE3)/pJA3.085, which carries a phlACBDE plasmid insert, synthesizes phloroglucinol and 2-acetylphloroglucinol but no 2,4-diacetylphloroglucinol (entry 3, Table 1). The absence of the phlE-encoded product exporter in *E. coli* Bl21(DE3)/pJA3.156 does not have an adverse impact on the concentrations of biosynthesized phloroglucinol 1a and 2-acetylphloroglucinol 2 (entry 4, Table 1). Product formation attendant with heterologous expression of only phlD is then evaluated using *E. coli* BL21(DE3)/pJA2.042 (entry 5, Table 1). Only phloroglucinol 1a formation is observed. The differences in the concentrations of phloroglucinol 1a biosynthesized by *E. coli* BL21(DE3)/pJA2.042 relative to *E. coli* Bl21(DE3)/pJA3.156 (entry 4 vs. entry 5, Table 1) likely reflect the proximity of phlD to the T7 promoter. Synthesis of phloroglucinol from glucose in minimal salts medium under fermentor-controlled conditions is examined using *E. coli* JWF1(DE3)/pJA3.131A (entry 6, Table 1).

To further explore its role in phloroglucinol biosynthesis, PhlD is purified to homogeneity and its in vitro enzymology examined. No activity (Table 1) is observed when acetyl-CoA alone is employed as a substrate. Approximately equal specific activities are observed when malonyl-CoA and acetyl-CoA are incubated with PhlD relative to incubation of PhlD with only malonyl-CoA. A $K_m$=37 µM for malonyl-CoA and a $k_{cat}$=4.7 min$^{-1}$ are determined for PhlD. For comparison, 2-pyrone synthase, which like PhlD employs an activated 3,5-diketohexanoate 2 (Scheme 1), is purified to homogeneity. 2-Pyrone synthase is unable to use acetyl-CoA as a substrate. However, incubation of 2-pyrone synthase with malonyl-CoA and acetyl-CoA yields twofold higher specific activities relative to incubation with malonyl-CoA in the absence of acetyl-CoA. Kinetic parameters for 2-pyrone synthase include $K_m$=XX µM for malonyl-CoA, $K_m$=2.2 µM for acetyl-CoA, and a $k_{cat}$=3.3 min$^{-1}$.

The products that form upon heterologous expression of PhlACBDE and PhlD raises the possibility that cyclization of an activated 3,5-diketohexanoate 2 (Scheme 1) and subsequent stepwise acetylation of phloroglucinol 1a might be the basis for biosynthesis of 2-acetylphloroglucinol 6 and 2,4-diacetylphloroglucinol 7. To further explore this possibility, *E. coli* BL21(DE3)/pJA3.169 is constructed with plasmid-localized phlACB. M. G. Bangera & L. S. Thomashow, *J. Bacteriol.* 181:3155 (1999). No phloroglucinols are synthesized upon culturing (entry 7, Table 8) of this construct, which lacks plasmid-localized phlD. However, addition of phloroglucinol 1a to the culture medium of *E. coli* BL21(DE3)/pJA3.169 does result in formation of 2-acetylphlorogluconol 6 and small amounts of 2,4-diacetylphloroglucinol 7 (entry 8, Table 1).

Figure 2:
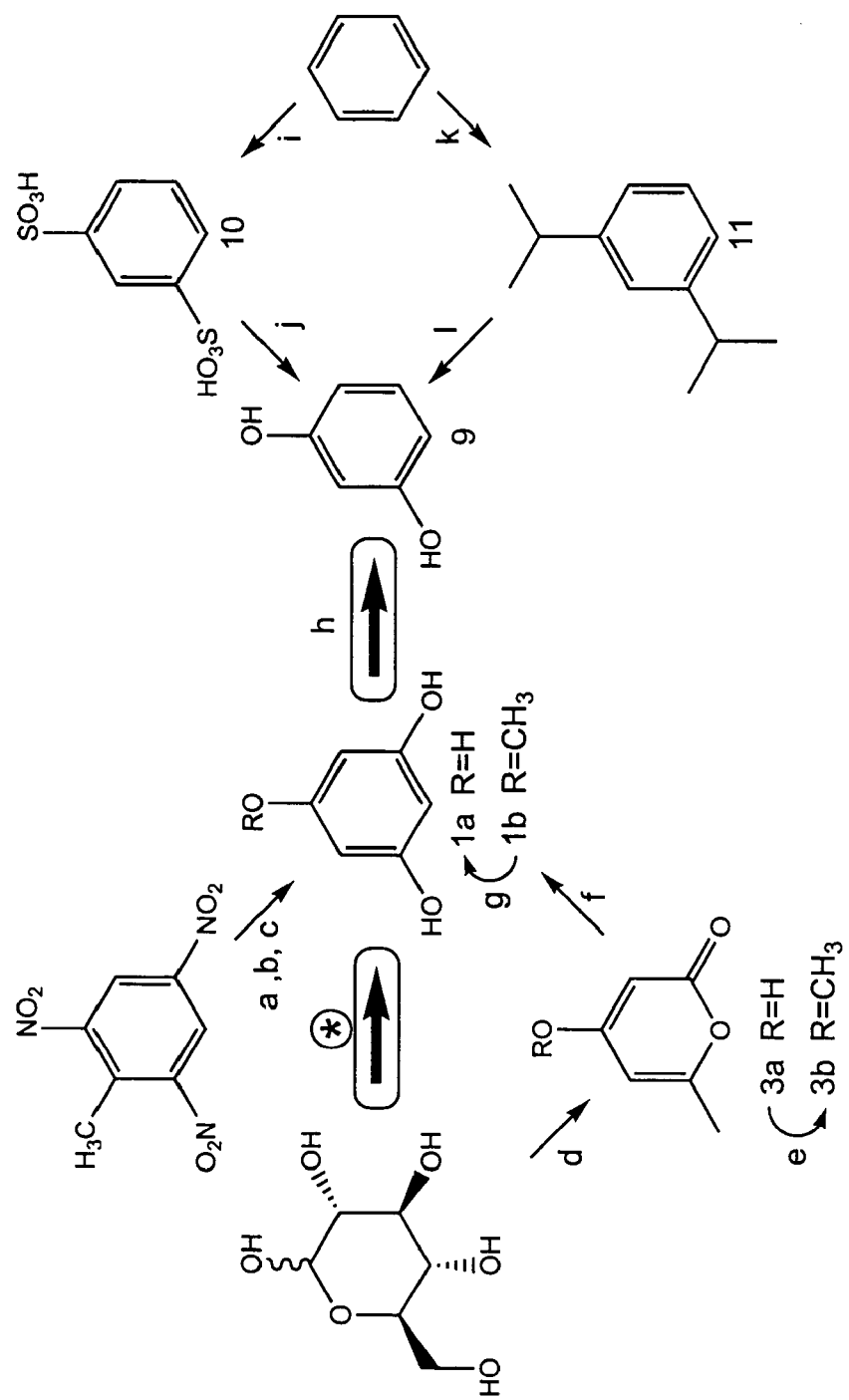
FIG. 2 presents Scheme 2, which illustrates: the common commercial chemical synthetic route (a, b, c) for phloroglucinol synthesis; a multi-step route (d, e, f, g) previously proposed for synthesis of phloroglucinol from glucose; a first, common commercial chemical synthetic route (i, j) for resorcinol synthesis; and a second, common commercial chemical synthetic route (k, l) for resorcinol synthesis. Also illustrated with circled arrows are: (1) the fully biosynthetic route reported in the present work (indicated by a circled asterisk) for production of phloroglucinol; and (2) the chemical hydrogenation (h) of phloroglucinol to resorcinol. Specific reactions or reaction steps shown are: (a) $Na_2Cr_2O_7$, $H_2SO_4$; (b) Fe, HCl; (c) $H_2SO_4$, 108° C.; (d) see W. Zha et al., *J. Am. Chem. Soc.* 126:4534 (2004); (e) Dowex 50 H$^+$, MeOH; (f) Na, MeOH, 185° C.; (g) 12N HCl; (h) i) $H_2$, Rh on $Al_2O_3$, ii) 0.5 M H$^2SO_4$, reflux; (i) $SO_3$, $H_2SO_4$; (j) NaOH, 350° C.; (k) HZSM-12 zeolite, propene; and (l) i) $O_2$, ii) $H_2O_2$, iii) H$^+$.

PhlD is also of particular importance in establishing the outline of a new synthesis of phloroglucinol, which is currently synthesized (Scheme 2, i.e. FIG. 2) from 2,4,6-trinitrotoluene 8 by a route involving an oxidation utilizing $Na_2Cr_2O_7$. G. Leston, In *Kirk-Othmer Encyclopedia of Chemical Technology*, Vol. 19, p 778 (J. I. Kroschwitz & M. Howe-Grant, eds.) (4th ed., 1996) (Wiley: New York). Beyond the explosion hazard, environmentally problematic chromates are generated as waste streams during synthesis of phloroglucinol 1a from 2,4,6-trinitrotoluene 8. Recently, an alternate route (Scheme 2) to phloroglucinol 1a has been elaborated involving microbe-catalyzed synthesis of triacetic acid lactone 3a. W. Zha et al., *J. Am. Chem. Soc.* 126:4534 (2004). Multiple chemical steps are needed to convert triacetic acid lactone 3a into phloroglucinol 1a. C. A Hansen & J. W. Frost, *J. Am. Chem. Soc.* 124:5926 (2002). In contrast to these chemical and chemoenzymatic routes to phlorogluci nol, heterologous expression of PhlD in *E. coli* allows phloroglucinol 1a to be made in a single microbe-catalyzed step from glucose (Scheme 2).

An alternative synthesis of resorcinol 9 is also now possible. Resorcinol is currently manufactured (Scheme 2) by alkali fusion of 1,3-benzenedisulfonic acid 10 or hydroperoxidation of 1,3-diisopropylbenzene 11. Alkali fusion requires high temperatures and generates large salt waste streams. Acetone hydroperoxide formed during hydroperoxidation is an explosion hazard. See L. Krumenacker et al., In *Kirk-Othmer Encyclopedia of Chemical Technology*, Vol. 13, p 996 (J. I. Kroschwitz & M. Howe-Grant, eds.) (4th ed., 1995) (Wiley: New York). In addition, both 1,3-benzenedisulfonic acid 10 and 1,3-diisopropylbenzene 11 are produced from petroleum-derived, carcinogenic benzene (Scheme 2). The new route to resorcinol 9 is based on the microbial synthesis of phloroglucinol 1a followed by Rh-catalyzed hydrogenation (Scheme 2) of this intermediate. C. A Hansen & J. W. Frost, *J. Am. Chem. Soc.* 124:5926 (2002). Since phloroglucinol 1a can now be synthesized from glucose, resorcinol joins catechol and hydroquinone as dihydroxy aromatics that are amenable to synthesis from nontoxic, plant-derived glucose (Scheme 2). See, respectively: K. D. Draths & J. W. Frost, *J. Am, Chem. Soc.* 117:2395 (1995); and N. Ran et al., *J. Am. Chem. Soc.* 123:10927 (2001).

Example 2

Expression of PhlD in *E. coli* Strains and Resulting Phloroglucinol Synthesis

Plasmid pJA3.131A (Kan$^R$, lacI$^Q$, $P_{T7}$-phlD, serA) is transfected into chromosomally serA$^-$ *E. coli* strains BL21(DE3), W3110(DE3), and JWF1(DE3) [i.e. RB791serA$^-$(DE3)], and into strain KL3(DE3) [i.e. AB2834(serA::aroB)] (*E. coli* strains RB791 and AB2834 are available from the *E. coli* Genetic Stock Center, New Haven, Conn., USA). All DE3 strains are obtained by integration of λDE3 prophage into the cell chromosomes. Cells are cultured in fed-batch conditions under mineral salts and limited glucose. Although all transformed strains express substantial levels of phloroglucinol, the BL21 and W3110 strains produce superior titers of 3.0 and 3.1 g/L phloroglucinol, respectively; and, relative to the amounts of glucose supplied to the cultures, these strains produce a superior phloroglucinol yields of 4.4 and 3.1 moles phloroglucinol per 100 moles of glucose (% mol/mol).

These tests also compare phloroglucinol expression levels in BL21 strains similarly transformed with a plasmid in which phlD is under the control of Ptac or $P_{T5}$; $P_{T7}$ is found to provide superior results (data not shown). In these tests, phloroglucinol accumulation for all strains stops increasing during the stationary (or maintenance) phase. For BL21 and W3110, the highest phloroglucinol concentration is achieved about 6 hours and about 12 hours, respectively, after initiation of induction, i.e. the first IPTG addition. End-product inhibition is also observed. Further tests demonstrate that phloroglucinol is responsible for the inhibition when at or above about 2 g/L concentration (data not shown).

Example 3

Extractive Phloroglucinol Fermentation

An anion-exchange resin column-based extractive fermentation is employed to remove phloroglucinol in order to reduce or eliminate its cytotoxicity and phloroglucinol synthesis repression during fermentation. A stirred tank reactor is equipped with tubing leading through an anion exchange column and returning to the tank; the tubing is equipped with a peristaltic pump in order to circulate the medium through the column. Bio-Rad Econo columns (25×200 mm) packed with 80 mL (bed volume) AG 1-X8 resin are rinsed with 15 bed volumes of $KH_2PO_4$ (0.8 M) to change the tertiary ammonium salts to phosphate form before the in situ extraction. A total of 3 to 5 columns are used for each fermentation; each column is used for about 6-12 h before being replaced with another column, in order to keep the culture medium's phloroglucinol concentration below about 1.5 g/L. All columns are operated in a fluidized-bed mode and the circulation flow rate is about 8-12 mL/min.

To recover the phloroglucinol adsorbed on the AG 1-X8 resin, the column is washed in a fluidized-bed mode with 10 bed volumes of distilled, deionized water to remove residual cells; this also recovers about 15% of the phloroglucinol from the resin, in the water solution. Then, the column is rinsed in a fixed-bed mode with 15 bed volumes of acidic ethanol (acetic acid, 10% (v/v); ethanol, 75% (v/v); $H_2O$, 15% (v/v)) to recover remaining phloroglucinol from the resin, in the acidic ethanol solution. After phloroglucinol recovery, the column can be regenerated by further rinses of 15 bed volumes of $KH_2PO_4$ (0.8 M), 2 bed volumes of ethanol (70%), and 5 bed volumes of sterilized distilled, deionized water, respectively.

To purify the recovered phloroglucinol, cells in the resulting water solution are removed by centrifugation; the solution is then concentrated to about 1/10 of the original volume. Separately, the acidic ethanol solution is concentrated to dryness. This residue is redissolved with the concentrated water solution. The resulting aqueous phase is then extracted three times with an equal volume of ethyl acetate. The organic phases are combined, dried over $MgSO_4$, mixed with silicone gel, concentrated to dryness, and loaded onto a flash column. Phloroglucinol is separated form other brown impurities by rinsing with hexane:acetate (1:1) and identified by TCL. The fraction containing phloroglucinol is then concentrated to dryness and dried under high vacuum conditions to afford phloroglucinol as pale crystals.

Example 4

Optimization of Phloroglucinol Fermentation

A variety of dual temperature fermentation profiles are used in extractive and non-extractive fermentations of the transformed W3110 strain described above. Glucose is steadily fed by $pO_2$ cascade control and the exhausted $CO_2$ level is maintained at a steady level until the end of the fermentation. In both types of fermentations, lowering the initial 36° C. temperature, during fermentation, is found to significantly increase the titer and yield of phloroglucinol, with extractive fermentation results being much greater. Temperature shifts to 30° C. are performed in separate fermentations at 12 h (the time of first induction by IPTG), 15 h (the beginning of maintenance phase), or 30 h. Superior results are obtained when the temperature shift occurs at 15 h and the extractive fermentation is permitted to proceed for a total of 60 h. Under these conditions, the W3110serA⁻(DE3)/pJA3.131A synthesizes 15 g/L phloroglucinol in a yield of 11% (mol/mol). In comparison with the non-extractive fermentation, the extractive fermentation is found to provide undiminished phloroglucinol production throughout the fermentation, a steady PhlD specific activity, maintained cell viability, and longer maximum fermentation times.

An identical fermentation profile, with identical extractive fermentation conditions, is also used to test phloroglucinol production by the BL21serA⁻ (DE3)/pJA3.131A strain described above. Equivalent results to those of the W3110 fermentation are obtained. One further dual temperature profile, in which the initial 36° C. temperature is shifted at 15 h to 33° C., is found to increase recovery of phloroglucinol from BL21 yet further, giving a 17.3 g/L titer and a 12.3% (mol/mol) yield.

In addition, expression of recombinant phlD in yeast, *S. cerevisiae*, is successful, although yields are from 0.5 to about 1.5 mg/L under test conditions (data not shown).

The examples and other embodiments described herein are exemplary and not intended to be limiting in describing the full scope of compositions and methods of this invention. Equivalent changes, modifications and variations of specific embodiments, materials, compositions and methods may be made within the scope of the present invention, with substantially similar results.

The invention claimed is:

1. A process for producing anabolic phloroglucinol, comprising the steps of
   (A) providing
   (1) an isolated recombinant cell comprising a phloroglucinol synthase having the amino acid sequence of SEQ ID NO: 2, wherein the isolated recombinant cell does not express other active enzymes involved in the acetylphloroglucinol synthesis pathway, the recombinant cell being capable of converting malonyl-CoA to phloroglucinol; and
   (2) malonyl-CoA; and
   (B) contacting the malonyl-CoA with the recombinant cell under conditions in which phloroglucinol can be synthesized therefrom;
   thereby producing anabolic phloroglucinol.

2. The process according to claim 1, wherein providing the isolated recombinant cell comprises introducing into a host cell, an isolated or recombinant nucleic acid vector comprising:
   at least one open reading frame encoding the phloroglucinol synthase having the amino acid sequence of SEQ ID NO: 2,
   wherein said nucleic acid vector does not express at least one of other active enzymes involved in the acetylphloroglucinol synthesis pathway.

3. The process according to claim 2, wherein said nucleic acid vector comprises the nucleic acid sequence of SEQ ID NO: 1, or a nucleic acid sequence encoding the amino acid sequence of SEQ ID NO: 2 and having at least one redundant codon therewith.

4. The process according to claim 2, wherein said nucleic acid vector comprises a nucleic acid sequence encoding SEQ ID NO: 2 which is at least 80% identical to SEQ ID NO: 1.

5. The process according to claim 1, wherein in the providing step, the malonyl-CoA is converted by the isolated recombinant cell from another carbon source.

6. The process according to claim 5, wherein said isolated recombinant cell further comprises at least one enzyme of the malonyl-CoA synthesis pathway for converting said carbon source to malonyl-CoA.

7. The process according to claim 6, wherein the enzyme of the malonyl-CoA synthesis pathway is any one of malonyl-CoA synthetase, malonyl-CoA decarboxylase, or acetyl-CoA carboxylase.

8. The process according to claim 5, wherein said carbon source comprises a saccharide, an aliphatic polyol, or a combination thereof.

9. The process according to claim 5, wherein said carbon source comprises glucose, xylose, arabinose, glycerol, or a combination thereof.

10. The process according to claim 5, wherein said contacting step comprises culturing the isolated recombinant cell in a growth medium containing the carbon source.

11. The process according to claim 10, wherein said culturing is performed as an extractive fermentation.

12. The process according to claim 1, further comprising modifying said anabolic phloroglucinol to prepare a derivative or composition thereof.

13. The process according to claim 12, wherein said derivative is resorcinol and wherein said modifying step comprises subjecting said anabolic phloroglucinol produced therefrom to a hydrogenation reaction, thereby obtaining resorcinol.

14. The process according to claim 13, wherein said subjecting step includes contacting said anabolic phloroglucinol with hydrogen and a rhodium catalyst, under conditions in which the phloroglucinol is capable of being hydrogenated to form resorcinol.

15. The process according to claim 12, wherein said composition is an explosive, propellant, medicament, cosmetic, dye, polymer resin, rubber, adhesive, sealant, coating, composite material, or laminated or bonded material.

* * * * *

UNITED STATES PATENT AND TRADEMARK OFFICE
CERTIFICATE OF CORRECTION

PATENT NO. : 8,329,445 B2
APPLICATION NO. : 13/081993
DATED : December 11, 2012
INVENTOR(S) : Frost It is certified that error appears in the above-identified patent and that said Letters Patent is hereby corrected as shown below:

In the Specification:

Column 1, Line 18, delete "STATEMENT OF GOVERNMENT INTEREST This invention was made with Government support under Grant No. N00014-02-1-0725, awarded by the Office of Naval Research. The government may have certain rights in this invention." and insert therefor

--GOVERNMENT LICENSE RIGHTS

This invention was made with government support under N00014-02-1-0725 awarded by the Office of Naval Research. The government has certain rights in the invention.--

Column 2, Line 38, delete "phioroglucinols" and insert therefor --phloroglucinols--

Column 2, Line 53, delete "phioroglucinols" and insert therefor --phloroglucinols--

Column 3, Line 44, delete "therein;," and insert therefor --therein,--

Column 5, Line 34, delete "$H^2SO_4$" and inset therefor --$H_2SO_4$--

Column 5, Line 64, after "itself" insert --.--

Column 6, Line 27, after "thereof" insert --.--

Column 6, Lines 49-50, delete "combinations the stated of features." and insert therefor --combinations of the stated features.--

Column 9, Line 55, delete "malonyl CoA" and insert therefor --malonyl-CoA--

Column 9, Line 57, delete "malonyl CoA" and insert therefor --malonyl-CoA--

Signed and Sealed this
Thirteenth Day of May, 2014

Michelle K. Lee
*Deputy Director of the United States Patent and Trademark Office*

CERTIFICATE OF CORRECTION (continued)
U.S. Pat. No. 8,329,445 B2

Column 12, Line 56, after "removal" insert --of--

Column 13, Line 32, delete "decrease" and insert therefor --decreased--

Column 13, Line 65, delete "*E. coiI*" and insert therefor --*E. coli*--

Column 14, Line 48, after "phloroglucinol" insert --.--

Column 15, Line 33, delete "therefore" and insert therefor --therefor--

Column 16, Line 3, delete "*Chem,*" and insert therefor --*Chem.*--

Column 16, Line 12, delete "*Microbial.*" and insert therefor --*Microbiol.*--

Column 16, Line 15, after "PhID" insert --has--

Column 16, Line 28, delete "PF-5" and insert therefor --Pf-5--

Column 16, Line 65, delete "*coiI*" and insert therefor --*coli*--

Column 17, Line 65, delete "C. A Hansen" and insert therefor --C. A. Hansen--

Column 18, Line 19, delete "C. A Hansen" and insert therefor --C. A. Hansen--

Column 18, Line 24, delete "*Am,*" and insert therefor --*Am.*--

Column 19, Line 38, delete "form" and insert therefor --from--

In the Claims:

Column 26, Line 6, Claim 17, delete "ofmalonyl-CoA" and insert therefor --of malonyl-CoA--

UNITED STATES PATENT AND TRADEMARK OFFICE
CERTIFICATE OF CORRECTION

| | | Page 1 of 2 |
|---|---|---|
| PATENT NO. | : 8,329,445 B2 | |
| APPLICATION NO. | : 13/081993 | |
| DATED | : December 11, 2012 | |
| INVENTOR(S) | : Frost | |

It is certified that error appears in the above-identified patent and that said Letters Patent is hereby corrected as shown below:

In the Specification:

Column 1, Line 18, delete "STATEMENT OF GOVERNMENT INTEREST This invention was made with Government support under Grant No. N00014-02-1-0725, awarded by the Office of Naval Research. The government may have certain rights in this invention." and insert therefor

--GOVERNMENT LICENSE RIGHTS

This invention was made with government support under N00014-02-1-0725 awarded by the Office of Naval Research. The government has certain rights in the invention.--

Column 2, Line 38, delete "phioroglucinols" and insert therefor --phloroglucinols--

Column 2, Line 53, delete "phioroglucinols" and insert therefor --phloroglucinols--

Column 3, Line 44, delete "therein;," and insert therefor --therein,--

Column 5, Line 34, delete "$H^2SO_4$" and inset therefor --$H_2SO_4$--

Column 5, Line 64, after "itself" insert --.--

Column 6, Line 27, after "thereof" insert --.--

Column 6, Lines 49-50, delete "combinations the stated of features." and insert therefor --combinations of the stated features.--

Column 9, Line 55, delete "malonyl CoA" and insert therefor --malonyl-CoA--

This certificate supersedes the Certificate of Correction issued May 13, 2014.

Signed and Sealed this
Tenth Day of June, 2014

Michelle K. Lee
*Deputy Director of the United States Patent and Trademark Office*

CERTIFICATE OF CORRECTION (continued)
U.S. Pat. No. 8,329,445 B2

Column 9, Line 57, delete "malonyl CoA" and insert therefor --malonyl-CoA--

Column 12, Line 56, after "removal" insert --of--

Column 13, Line 32, delete "decrease" and insert therefor --decreased--

Column 13, Line 65, delete "*E. coil*" and insert therefor --*E. coli*--

Column 14, Line 48, after "phloroglucinol" insert --.--

Column 15, Line 33, delete "therefore" and insert therefor --therefor--

Column 16, Line 3, delete "*Chem,*" and insert therefor --*Chem.*--

Column 16, Line 12, delete "*Microbial.*" and insert therefor --*Microbiol.*--

Column 16, Line 15, after "PhlD" insert --has--

Column 16, Line 28, delete "PF-5" and insert therefor --Pf-5--

Column 16, Line 65, delete "*coil*" and insert therefor --*coli*--

Column 17, Line 65, delete "C. A Hansen" and insert therefor --C. A. Hansen--

Column 18, Line 19, delete "C. A Hansen" and insert therefor --C. A. Hansen--

Column 18, Line 24, delete "*Am,*" and insert therefor --*Am.*--

Column 19, Line 38, delete "form" and insert therefor --from--

In the Claims:

Column 26, Line 6, Claim 7, delete "ofmalonyl-CoA" and insert therefor --of malonyl-CoA--